United States Patent
Fynbo et al.

(10) Patent No.: US 8,722,620 B2
(45) Date of Patent: May 13, 2014

(54) INSULIN DERIVATIVES

(75) Inventors: Charlotte Harkjaer Fynbo, Herlev (DK); Ib Jonassen, Valby (DK); Thomas Børglum Kjeldsen, Virum (DK); Peter Madsen, Bagsvaerd (DK); Patrick William Garibay, Holte (DK); Janos Tibor Kodra, Copenhagen (DK); Thomas Hoeg-Jensen, Klampenborg (DK); Tina Møller Tagmose, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 348 days.

(21) Appl. No.: 12/280,851

(22) PCT Filed: Feb. 27, 2007

(86) PCT No.: PCT/EP2007/051835
§ 371 (c)(1),
(2), (4) Date: Oct. 8, 2008

(87) PCT Pub. No.: WO2007/096431
PCT Pub. Date: Aug. 30, 2007

(65) Prior Publication Data
US 2009/0137454 A1 May 28, 2009

Related U.S. Application Data

(60) Provisional application No. 60/777,765, filed on Mar. 1, 2006.

(30) Foreign Application Priority Data

Feb. 27, 2006 (EP) .................................... 06110441
Aug. 1, 2006 (EP) .................................... 06118253

(51) Int. Cl.
*A61K 38/28* (2006.01)
*A61P 3/10* (2006.01)

(52) U.S. Cl.
USPC ............... 514/5.9; 514/6.1; 514/6.2; 514/6.3; 514/6.9

(58) Field of Classification Search
None
See application file for complete search history.

(56) References Cited

U.S. PATENT DOCUMENTS

| | | | |
|---|---|---|---|
| 5,650,486 A * | 7/1997 | De Felippis | ................ 530/305 |
| 5,750,497 A | 5/1998 | Havelund et al. | |
| 5,898,067 A | 4/1999 | Balschmidt et al. | |
| 5,905,140 A | 5/1999 | Hansen | |
| 6,011,007 A | 1/2000 | Havelund et al. | |
| 6,174,856 B1 | 1/2001 | Langballe et al. | |
| 6,451,762 B1 * | 9/2002 | Havelund et al. | ................ 514/3 |
| 6,451,970 B1 | 9/2002 | Schaffer et al. | |
| 6,620,780 B2 | 9/2003 | Markussen et al. | |
| 6,869,930 B1 | 3/2005 | Havelund et al. | |
| 7,229,964 B2 | 6/2007 | Markussen et al. | |
| 7,615,532 B2 | 11/2009 | Jonassen et al. | |
| 8,003,605 B2 | 8/2011 | Bayer et al. | |
| 8,067,362 B2 | 11/2011 | Kodra et al. | |
| 2004/0138099 A1 | 7/2004 | Draeger | |
| 2006/0183667 A1 | 8/2006 | Jonassen et al. | |
| 2006/0217290 A1 * | 9/2006 | Kohn et al. | ................ 514/3 |
| 2009/0074882 A1 | 3/2009 | Havelund et al. | |
| 2009/0105121 A1 | 4/2009 | Jonassen et al. | |
| 2009/0239784 A1 | 9/2009 | Jonassen et al. | |
| 2009/0239785 A1 | 9/2009 | Hubalek et al. | |
| 2010/0009899 A1 | 1/2010 | Jonassen et al. | |
| 2010/0167990 A1 | 7/2010 | Poulsen et al. | |
| 2010/0279931 A1 | 11/2010 | Garibay et al. | |
| 2011/0230402 A1 | 9/2011 | Johansen et al. | |
| 2011/0245163 A1 | 10/2011 | Jonassen et al. | |
| 2012/0035104 A1 | 2/2012 | Kodra et al. | |

FOREIGN PATENT DOCUMENTS

| | | |
|---|---|---|
| JP | 2002-518408 A | 6/2002 |
| JP | 2003-525846 A | 9/2003 |
| JP | 2005-526009 A | 9/2005 |
| WO | WO 95/07931 | 3/1995 |
| WO | WO 96/15803 | 5/1996 |
| WO | WO 96/29344 | 9/1996 |
| WO | WO 97/31022 | 8/1997 |
| WO | WO 99/65941 | 12/1999 |
| WO | WO 03/048195 | 6/2003 |
| WO | WO 2005/005477 | 1/2005 |
| WO | WO 2005/012347 | 2/2005 |
| WO | WO 2005/047508 | 5/2005 |
| WO | WO 2006/008238 | 1/2006 |
| WO | WO 2006/082204 | 8/2006 |
| WO | WO 2007/074133 | 7/2007 |
| WO | 2007/096431 A1 | 8/2007 |
| WO | WO 2007/128815 | 11/2007 |
| WO | WO 2007/128817 | 11/2007 |
| WO | WO 2008/152106 | 12/2008 |
| WO | WO 2009/060071 | 5/2009 |
| WO | WO 2009/063072 | 5/2009 |
| WO | WO 2010/049488 | 5/2010 |
| WO | 2011/141407 A1 | 11/2011 |

OTHER PUBLICATIONS

Olsen et al., Biochemistry, 39:11893-11900, 2000.*
Bhatnagar, S. et al., Progress in Biophysics and Molecular Biology, 2006, pp. 199-228, vol. 91, Pt. 3.
Hashimoto, M. et al., Pharmaceutical Research, 1989, pp. 171-176, vol. 6, Pt 2.

* cited by examiner

*Primary Examiner* — Gyan Chandra
(74) *Attorney, Agent, or Firm* — Michael J. Brignati

(57) ABSTRACT

The present invention is related to insulin derivatives having a side chain attached to an ε-amino group of a Lys residue present in the A-chain or to an ε-amino group of a Lys residue in the B-chain.

29 Claims, No Drawings

INSULIN DERIVATIVES

CROSS-REFERENCE TO RELATED APPLICATIONS

This application is a 35 U.S.C. §371 national stage application of International Patent Application PCT/EP2007/051835 (published as WO 2007/096431 A1), filed, which claimed priority of European Patent Application 06110441.0, filed Feb. 27, 2006 and European Patent Application 06118253.1, filed Aug. 1, 2006; this application further claims priority under 35 U.S.C. §119 of U.S. Provisional Application 60/777,765, filed Mar. 1, 2006.

FIELD OF THE INVENTION

The present invention relates to novel human insulin derivatives which are soluble at physiological pH values and have a prolonged profile of action. The invention also relates to pharmaceutical compositions containing them, to a method of treating diabetes and hyperglycaemia using the insulin derivatives of the invention and to the use of such insulin derivatives in the treatment of diabetes and hyperglycaemia.

BACKGROUND OF THE INVENTION

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of long acting insulin to cover the basal insulin requirement supplemented by bolus injections of a rapid acting insulin to cover the insulin requirement related to meals.

Long acting insulin compositions are well known in the art. Thus, one main type of long acting insulin compositions comprises injectable aqueous suspensions of insulin crystals or amorphous insulin. In these compositions, the insulin compounds utilized typically are protamine insulin, zinc insulin or protamine zinc insulin.

Certain drawbacks are associated with the use of insulin suspensions. Thus, in order to secure an accurate dosing, the insulin particles must be suspended homogeneously by gentle shaking before a defined volume of the suspension is withdrawn from a vial or expelled from a cartridge. Also, for the storage of insulin suspensions, the temperature must be kept within more narrow limits than for insulin solutions in order to avoid lump formation or coagulation.

Another type of long acting insulin compositions are solutions having a pH value below physiological pH from which the insulin will precipitate because of the rise in the pH value when the solution is injected. A drawback with these solutions is that the particle size distribution of the precipitate formed in the tissue on injection, and thus the release profile of the medication, depends on the blood flow at the injection site and other parameters in a somewhat unpredictable manner. A further drawback is that the solid particles of the insulin may act as a local irritant causing inflammation of the tissue at the site of injection.

Human insulin has three primary amino groups: the N-terminal group of the A-chain and of the B-chain and the ε-amino group of LysB29. Several insulin derivatives which are substituted in one or more of these groups are known in the prior art.

WO 95/07931 (Novo Nordisk A/S) discloses human insulin derivatives wherein the ε-amino group of LysB29 has a lipophilic substituent. These insulin derivatives have a prolonged profile of action and are soluble at physiological pH values.

International patent application WO 96/29344 concerns an insulin derivative, where a lipofilic sidechain is attached to the N-terminal amino group of B-chain or a Lys residue at position B26-B29 of the parent insulin molecule.

WO 97/31022 discloses insulin derivatives wherein the α-amino group of N-terminal group of the B-chain and/or the ε-amino group of Lys at position B28, B29 or B30 has a substituent of the formula —CO—W—COOH where W is be a long chain hydrocarbon group having from 12 to 22 carbon atoms. These insulin derivatives have a prolonged profile of action and are soluble at physiological pH values.

Another insulin derivative is disclosed in international patent application. The application patent application WO 2005/012347 describes an insulin derivative having a side chain attached to either the α-amino group of the N-terminal amino acid residue of the B-chain or to the ε-amino acid of a Lys residue present in the B-chain of the parent insulin.

Unfortunately, many diabetics are unwilling to undertake intensive therapy due to the discomfort associated with the many injections required to maintain close control of glucose levels. This type of therapy can be both psychologically and physically painful. Upon oral administration, insulin is rapidly degraded in the gastro intestinal tract and is not absorbed into the blood stream. Therefore, many investigators have studied alternate routes for administering insulin, such as oral, rectal, transdermal, and nasal routes. Thus far, however, these routes of administration have not resulted in effective insulin absorption.

Efficient pulmonary delivery of a protein is dependent on the ability to deliver the protein to the deep lung alveolar epithelium. Proteins that are deposited in the upper airway epithelium are not absorbed to a significant extent. This is due to the overlying mucus which is approximately 30-40 μm thick and acts as a barrier to absorption. In addition, proteins deposited on this epithelium are cleared by mucociliary transport up the airways and then eliminated via the gastrointestinal tract. This mechanism also contributes substantially to the low absorption of some protein particles. The extent to which proteins are not absorbed and instead eliminated by these routes depends on their solubility, their size, as well as other less understood characteristics.

There is still a need for insulins having a more prolonged profile of action than the insulin derivatives known up till now and which at the same time are soluble at physiological pH values and have a potency which is comparable to that of human insulin. Furthermore, there is need for further insulin formulations which are well suited for pulmonary application.

The present invention addresses and alleviates the problems of the prior art.

SUMMARY OF THE INVENTION

The present invention is based on the recognition that acylation of insulin can be performed in a Lys residue present in the A-chain or in a Lys residue in the B-chain of a parent insulin.

According to the invention there is provided an insulin derivative comprising a parent insulin and a substituent, wherein the substituent is attached either to an ε-amino group of a Lys residue present in the A-chain of the parent insulin at position A8, A9, A10, A12, A14, A15, A17, A18, A21, A22, A23 or A24 or to an ε-amino group of a Lys residue in the B-chain of the parent insulin at position B1, B2, B3, B4, B20, B21 or B22 provided that when B3 is Lys, then B29 is not Glu.

The substituent attached to ε-amino group of the Lys residue can comprise a lipophilic group, a fatty acid or a fatty diacid, an aromatic group or an amino acid residue which optionally contains a group which can be negatively charged.

The fatty diacid will typically comprise from 4 to 22, from 6 to 22, from 8 to 20, from 8 to 18, from 4 to 18, from 6 to 18, from 8 to 16, from 8 to 22, from 8 to 17 or from 8 to 15 carbon atoms in the carbon chain.

Non limiting examples of the fatty diacid moiety are diacids with the formula $HOOC-(CH_2)_{r_1}-COOH$, where $r_1$ is 4 to 22. Examples of fatty diacids are succinic acid, hexanedioic acid, octanedioic acid, decanedioic acid, dodecanedioic acid, tetradecanedioic acid, hexadecanedioic acid or octadecandedioic acid.

DEFINITIONS

With "desB30 insulin", "desB30 human insulin" is meant a natural insulin or an analogue thereof lacking the B30 amino acid residue. Similarly, "desB29desB30 insulin" or "desB29desB30 human insulin" means a natural insulin or an analogue thereof lacking the B29 and B30 amino acid residues.

With "B(1-29)" and "B-chain" is meant a natural insulin B-chain or an analogue thereof lacking the B30 amino acid residue. "A(1-21)" and "A-chain" means the natural insulin A-chain or an analogue thereof. "A(1-24) means a modified A-chain, where the A-chain has been extended at the C-terminal with 3 codable amino acids.

With "B1", "A1" etc. is meant the amino acid residue at position 1 in the B-chain of insulin (counted from the N-terminal end) and the amino acid residue at position 1 in the A-chain of insulin (counted from the N-terminal end), respectively. The amino acid residue in a specific position may also be denoted as e.g. PheB1 which means that the amino acid residue at position B1 is a phenylalanine residue.

With "insulin" as used herein is meant human insulin with disulfide bridges between CysA7 and CysB7 and between CysA20 and CysB19 and an internal disulfide bridge between CysA6 and CysA11, porcine insulin and bovine insulin.

"POT" is the *Schizosaccharomyces pombe* triose phosphate isomerase gene.

By a "leader" is meant an amino acid sequence consisting of a pre-peptide (the signal peptide) and a pro-peptide.

The term "signal peptide" is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the yeast organism producing the protein. A number of signal peptides which may be used with the DNA construct of the invention including yeast aspartic protease 3 (YAP3) signal peptide or any functional analog (Egel-Mitani et al. (1990) YEAST 6:127-137 and U.S. Pat. No. 5,726,038) and the α-factor signal of the MFα1 gene (Thorner (1981) in The Molecular Biology of the Yeast *Saccharomyces cerevisiae*, Strathern et al., eds., pp 143-180, Cold Spring Harbor Laboratory, NY and U.S. Pat. No. 4,870,00.

The term "pro-peptide" means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast (X-factor pro-peptide, vide U.S. Pat. Nos. 4,546,082 and 4,870,008. Alternatively, the pro-peptide may be a synthetic propeptide, which is to say a pro-peptide not found in nature. Suitable synthetic pro-peptides are those disclosed in U.S. Pat. Nos. 5,395,922; 5,795,746; 5,162,498 and WO 98/32867. The pro-peptide can contain an endopeptidase processing site at the C-terminal end, such as a Lys-Arg sequence or any functional analogue thereof.

By "insulin precursor" as used herein is meant a single chain polypeptide which after cleavage with an appropriate protease, for example trypsin, yields a two chain insulin, insulin analogue, or insulin derivative. An example of such an insulin precursor is "B'A", which is a single chain insulin precursor where the C-terminal amino acid residue of the B-chain is directly bound to the A1 amino acid residue in the A-chain. A specific example of such a B'A insulin precursor is LysA9 ArgB29 desB30 B'A, where ArgB29 is directly connected to GlyA1.

By "insulin analogue" as used herein is meant a polypeptide which has a molecular structure which formally can be derived from the structure of a naturally occurring insulin, for example that of human insulin, by deleting and/or substituting at least one amino acid residue occurring in the natural insulin and/or by adding at least one amino acid residue. The added and/or substituted amino acid residues can either be codable amino acid residues or other naturally occurring amino acid residues or purely synthetic amino acid residues.

Examples of insulin analogues are desB30 human insulin analogues; insulin analogues wherein one or both of B1 and B2 have been deleted; insulin analogues wherein the A-chain and/or the B-chain have an N-terminal extension and insulin analogues wherein the A-chain and/or the B-chain have a C-terminal extension. Thus one or two Arg may be added to position B1. Also one or more of B26-B30 may have been deleted.

By "parent insulin" is meant an insulin analogue containing only one Lys residue in the A-chain and/or the B-chain, which Lys residue is not present at position B29.

Specific examples of parent insulins are LysA9 ArgB29 desB30 human insulin and LysB22 ArgB29 desB30 human insulin.

By "insulin derivative" as used herein is meant a naturally occurring insulin or an insulin analogue which has been chemically modified, e.g. by introducing a substituent in one or more positions of the insulin backbone or by oxidizing or reducing groups of the amino acid residues in the insulin or by converting a free carboxylic group to an ester group or acylating a free amino group or a hydroxy group.

The insulin derivatives of the invention are named according to the following rule: The sequence starts with the chemical modification, continues with the A-chain, and ends with the B-chain. The amino acid residues are named after their respective counterparts in human insulin and mutations and acylations are explicitly described whereas unaltered amino acid residues in the A- and B-chains are not mentioned. For example, an insulin having the following mutations as compared to human insulin LysA9, ArgB29, desB30 and is acylated with myristyl at the $N^\epsilon$ of LysA9 is named $N^{\epsilon A9}$-myristyl LysA9 ArgB29 desB30 human insulin.

When an insulin derivative according to the invention is stated to be "soluble at physiological pH values" it means that the insulin derivative can be used for preparing insulin compositions that are fully dissolved at physiological pH values. Such favourable solubility may either be due to the inherent properties of the insulin derivative alone or a result of a favourable interaction between the insulin derivative and one or more ingredients contained in the vehicle.

Abbreviations for Amino Acids:

| Amino acid | Three-letter code |
|---|---|
| Glycine | Gly |
| Proline | Pro |
| Alanine | Ala |
| Valine | Val |
| Leucine | Leu |
| Isoleucine | Ile |
| Methionine | Met |
| Cysteine | Cys |
| Phenylalanine | Phe |
| Tyrosine | Tyr |
| Tryptophan | Trp |
| Histidine | His |
| Lysine | Lys |
| Arginine | Arg |
| Glutamine | Gln |
| Asparagine | Asn |
| Glutamic Acid | Glu |
| Aspartic Acid | Asp |
| Serine | Ser |
| Threonine | Thr |

The expression "an amino acid residue having a carboxylic acid group in the side chain" designates amino acid residues like Asp, Glu and hGlu. The amino acids can be in either the L- or D-configuration. If nothing is specified it is understood that the amino acid residue is in the L-configuration.

The expression "an amino acid residue having a neutral side chain" designates amino acid residues like Gly, Ala, Val, Leu, Ile, Phe, Pro, Ser, Thr, Cys, Met, Tyr, Asn and Gln.

Abbreviations Used in the Examples:

| CV | column volume |
|---|---|
| EDTA | ethylene diamine tetraacetic acid |
| HI | human insulin |
| HPLC | High Performance Liquid Chromatography |
| HSA | human serum albumin |
| LC | liquid chromatography |
| MALDI | Matrix Assisted Laser Desorption Ionization |
| MS | mass spectrometry |
| NMP | N-methyl-2-pyrrolidone |
| PCR | polymerase chain reaction |
| PMSF | phenyl methyl sulphonyl fluoride |
| RT | room temperature |
| SEC | size exclusion chromatography |
| SPA | Scitillation Proximity Assay |
| Tris | tris(hydroxymethyl)aminomethane |
| vol % | volume percentage |
| O.D. | optical density = absorbance |
| X2 monomer | AspB9 GluB27 human insulin |
| hGlu | homo-glutamic acid |
| Su | N-succinimidyl | hGlu is homoglutamic acid.
TFA: trifluoracetic acid
DMF: N,N-dimethylformamide
EtOAc: Ethyl acetate
THF: tetrahydrofuran
TSTU: O—(N-succinimidyl)-1,1,3,3-tetramethyluronium tetrafluoroborate
DIPEA: Diisopropylethylamine
α-Asp is the L-form of —HNCH(CO—)CH$_2$COOH.
β-Asp is the L-form of —HNCH(COOH)CH$_2$CO—.
α-Glu is the L-form of —HNCH(CO—)CH$_2$CH$_2$COOH.
γ-Glu is the L-form of —HNCH(COOH)CH$_2$CH$_2$CO—.
α-hGlu is the L-form of —HNCH(CO—)CH$_2$CH$_2$CH$_2$COOH.
δ-hGlu is the L-form of —HNCH(COOH)CH$_2$CH$_2$CH$_2$CO—.
β-Ala is —NH—CH$_2$—CH$_2$—COOH.
Sar is sarcosine (N-methylglycine).

DETAILED DESCRIPTION OF THE INVENTION

The present invention concerns an insulin derivatives comprising a parent insulin and a substituent, wherein the substituent is attached either to an ε-amino group of a Lys residue present in the A-chain of the parent insulin at position A8, A9, A10, A12, A14, A15, A17, A18, A21, A22, A23 or A24 or to an ε-amino group of a Lys residue in the B-chain of the parent insulin at position B1, B2, B3, B4, B20, B21 or B22 provided that when B3 is Lys, then B29 is not Glu.

In one aspect the substituent of the insulin derivative according to the invention is attached to the ε-amino group of the Lys residue present at position A8 in the A-chain of the parent insulin.

In one aspect the substituent of the insulin derivative is attached to the ε-amino group of the Lys residue present at position A9 in the A-chain of the parent insulin.

In one aspect the substituent of the insulin derivative is attached to the ε-amino group of the Lys residue present at position A14 in the A-chain of the parent insulin.

In one aspect the substituent of the insulin derivative is attached to the ε-amino group of the Lys residue present at position A18 in the A-chain of the parent insulin.

In one aspect the substituent of the insulin derivative is attached to the ε-amino group of the Lys residue present at position A21 in the A-chain of the parent insulin.

In one aspect the substituent of the insulin derivative is attached to the ε-amino group of the Lys residue present at position A22 in the A-chain of the parent insulin.

In one aspect the substituent of the insulin derivative according to the invention is attached to the ε-amino group of the Lys residue present at position A23 in the A-chain of the parent insulin.

In one aspect the substituent of the insulin derivative according to the invention is attached to the ε-amino group of the Lys residue present at position A24 in the A-chain of the parent insulin.

The substituent at the lysine residue of the insulin derivative according to the invention can comprise a lipophilic group containing from 6 to 40 carbon atoms. Examples of substituents are acyl groups having from 6 to 40, for example 12 to 36, carbon atoms.

Examples of substituents are acyl groups having from 12 to 36 carbon atoms or lipophilic substituents in the form of acyl groups are the following: $CH_3—(CH_2)_n—CO—$, $(COOH)—(CH_2)_n—CO—$, $(NH_2—CO)—(CH_2)_n—CO—$, $HO—(CH_2)_n—CO—$, where $4 \leq n \leq 38$, for example where $6 \leq n \leq 36$, $8 \leq n \leq 34$, $12 \leq n \leq 32$ or $12 \leq n \leq 28$.

In one aspect of the invention the acyl group is 5-α lithocholic acid or 5-β lithocholic acid.

In one aspect the acyl group is 5-α or 5-β isomers of cholic acid, hyocholic acid, deoxycholic acid, chenodeoxycholic acid, ursodeoxycholic acid, hyodeoxycholic acid or cholanic acid.

In one aspect the acyl group is 5-α or 5-β isomers of dehydrolithocholic acid.

In one aspect the acyl group is fusidic acid, a fusidic acid derivative or glycyrrhetinic acid.

In one aspect the acyl group is connected to a lysine residue using an amino acid linker. According to this aspect the acyl group is advantageously connected to a lysine residue via a γ- or an α-glutamyl linker, or via a β- or an α-aspartyl linker, or via an α-amido-γ-glutamyl linker, or via an α-amido-β-aspartyl linker.

In one aspect of the invention the substituent of the insulin derivative has a general formula:

—W—X—Y—Z wherein W is:

an α-amino acid residue having a carboxylic acid group in the side chain which residue forms, with one of its carboxylic acid groups, an amide group with the ε-amino group of a Lys residue present in the A- or the B-chain of the parent insulin; or a chain composed of two, three or four α-amino acid residues linked together via amide bonds, which chain, via an amide bond, is linked to the ε-amino group of a Lys residue present in the A- or the B-chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or a covalent bond from X to the ε-amino group of a Lys residue present in the A- or the B-chain of the parent insulin;

X is:
—CO—;
—CH(COOH)CO—;
—CON(CH$_2$C$\overline{\text{O}}$OH)CH$_2$$\ddot{\text{C}}$O—;
—CON(CH$_2$COOH)CH$_2$CON(CH$_2$COOH)CH$_2$CO—;
—CON(CH$_2$CH$_2$COOH)CH$_2$CH$_2$CO—;
—CON(CH$_2$CH$_2$COOH)CH$_2$CH$_2$$\overline{\text{C}}$ON(CH$_2$CH$_2$COOH)CH$_2$CH$_2$CO—;
—CO$\overline{\text{N}}$HCH(COOH)(CH$_2$)$_4$NHCO—
—CON(CH$_2$CH$_2$COOH)CH$_2$$\overline{\text{CO}}$—; or
—CON(CH$_2$COOH)CH$_2$CH$_2$$\overline{\text{C}}$O—

Provided that a) when W is an amino acid residue or a chain of amino acid residues, the underscored carbonyl carbon in X forms an amide bond with an amino group in W, or b) when W is a covalent bond, the underscored carbonyl carbon in X forms an amide bond with the ε-amino group of a Lys residue present in the A- or the B-chain of the parent insulin;

Y is:
—(CH$_2$)$_m$— where m is an integer in the range of 6 to 32;
a divalent hydrocarbon chain comprising 1, 2 or 3 —CH═CH— groups and a number of —CH$_2$— groups sufficient to give a total number of carbon atoms in the chain in the range of 10 to 32;
a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and Z is:
—COOH;
—CO-Asp;
—CO-Glu;
—CO-Gly;
—CO-Ser;
—CH(COOH)$_2$;
—N(CH$_2$COOH)$_2$;
—SO$_3$H; or
—PO$_3$H;
and any Zn$^{2+}$ complexes thereof.

In one aspect of the invention, side chain —W—X—Y—Z is attached to the ε-amino group of a Lys residue present in the A- or B-chain of the parent insulin. In one more specific aspect of this aspect, the side chain —W—X—Y—Z is attached to the ε-amino group of a Lys residue present at position A8, A9, A10, A12, A14, A15, A17, A18, A21, A22, A23, A24 or B1, B2, B3, B4, B20, B21 or B22.

The substructure W of the substituent —W—X—Y—Z can be a covalent bond. Alternatively, W can be a residue of an amino acid having a carboxylic acid group in the side chain which residue forms, with one of its carboxylic acid groups, an amide group with the ε-amino group of a Lys residue present in the A- or the B-chain of the parent insulin and where said residue comprises a total of from 4 to 10 carbon atoms. Specifically, W can, for example, be a linker.

In one aspect W can be connected to the ε-amino group of the Lys residue in the A- or B-chain of the parent insulin via a urea linker.

In one aspect the linker comprises 1-4 amino acid residues linked together via amide bonds of which at least one has a free carboxylic acid group or a group which is negatively charged at neutral pH.

In one aspect the linker is an amino acid residue, a peptide chain of 2-4 amino acid residues or has the motif is α-Asp, β-Asp, α-Glu, γ-Glu, α-hGlu and δ-hGlu; —N(CH$_2$COOH)CH$_2$CO—;   —N(CH$_2$CH$_2$COOH)CH$_2$CH$_2$CO—; —N(CH$_2$COOH)CH$_2$CH$_2$CO— or —N(CH$_2$CH$_2$COOH)CH$_2$CO—.

The linkers will typically be an amino acid residue or a chain of amino acid residue comprising up to four amino acids. Specifically, the linker may be selected from the group consisting of α-Asp; β-Asp; α-Glu; γ-Glu; α-hGlu; δ-hGlu; —N(CH$_2$COOH)CH$_2$CO—, —N(CH$_2$CH$_2$COOH)CH$_2$CH$_2$CO—; —N(CH$_2$COOH)CH$_2$CH$_2$CO— or —N(CH$_2$CH$_2$COOH)CH$_2$CO—

In a further aspect the linker can be a chain composed of two amino acid residues of which one has from 4 to 10 carbon atoms and a carboxylic acid group in the side chain while the other has from 2 to 11 carbon atoms but no free carboxylic acid group. The amino acid residue with no free carboxylic acid group can be a neutral α-amino acid residue. Examples of such linkers are: α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

In a further aspect the linker is a chain composed of two amino acid residues, independently having from 4 to 10 carbon atoms, and both having a carboxylic acid group in the side chain. One of these amino acid residues or both of them can be α-amino acid residues. Examples of such linkers are: α-Asp-α-Asp; α-Asp-α-Glu; α-Asp-α-hGlu; α-Asp-β-Asp; α-Asp-γ-Glu; α-Asp-δ-hGlu; β-Asp-α-Asp; β-Asp-α-Glu; β-Asp-α-hGlu; β-Asp-β-Asp; β-Asp-γ-Glu; β-Asp-δ-hGlu; α-Glu-α-Asp; α-Glu-α-Glu; α-Glu-α-hGlu; α-Glu-β-Asp; α-Glu-γ-Glu; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-β-Asp; α-hGlu-γ-Glu; α-hGlu-δ-hGlu; δ-hGlu-α-Asp; δ-hGlu-α-Glu; δ-hGlu-α-hGlu; δ-hGlu-β-Asp; δ-hGlu-γ-Glu; and δ-hGlu-δ-hGlu.

In a further aspect the linker is a chain composed of three amino acid residues, independently having from 4 to 10 carbon atoms, the amino acid residues of the chain being selected from the group of residues having a neutral side chain and residues having a carboxylic acid group in the side chain so that the chain has at least one residue which has a carboxylic acid group in the side chain. In one aspect, the amino acid residues are α-amino acid residues.

In a further aspect, the linker is a chain composed of four amino acid residues, independently having from 4 to 10 carbon atoms, the amino acid residues of the chain being selected from the group having a neutral side chain and residues having a carboxylic acid group in the side chain so that the chain has at least one residue which has a carboxylic acid group in the side chain. In one aspect, the amino acid residues are α-amino acid residues.

The substructure X of the side chain —W—X—Y—Z can be a group of the formula —CO— that, which via a bond from the underscored carbonyl carbon in X, forms an amide bond with an amino group in W or, when W is a covalent bond, forms a bond with the ε-amino group of a Lys residue present in the A- or B-chain of the parent insulin.

In a further aspect, the substructure X of the side chain can be a group of the formula —COCH(COOH)CO— that, via a bond from the underscored carbonyl carbon in X, forms an amide bond with an amino group in W or, when W is a covalent bond, forms a bond with the ε-amino group of a Lys residue present in the A- or B-chain of the parent insulin.

In a further aspect, the substructure X of the side chain can be a group of the formula —CON(CH$_2$COOH)CH$_2$CO— that, via a bond from the underscored carbonyl carbon in X, forms an amide bond with an amino group in W or, when W is a covalent bond, forms a bond with the ε-amino group of a Lys residue present in the A- or B-chain of the parent insulin.

In a further aspect, the substructure X of the side chain can be a group of the formula —CON(CH$_2$COOH)CH$_2$CON(CH$_2$COOH)CH$_2$CO— that, via a bond from the underscored carbonyl carbon in X, forms an amide bond with an amino group in W or, when W is a covalent bond, forms a bond with the ε-amino group of a Lys residue present in the A- or B-chain of the parent insulin.

In a further aspect, the substructure X of the side chain can be a group of the formula —CON(CH$_2$CH$_2$COOH)CH$_2$CH$_2$CO— that, via a bond from the underscored carbonyl carbon in X, forms an amide bond with an amino group in W or, when W is a covalent bond, forms a bond with the ε-amino group of a Lys residue present in the A- or B-chain of the parent insulin.

In a further aspect, the substructure X of the side chain can be a group of the formula —CON(CH$_2$CH$_2$COOH)CH$_2$CH$_2$CON(CH$_2$CH$_2$COOH)CH$_2$CH$_2$CO— that, via a bond from the underscored carbonyl carbon in X, forms an amide bond with an amino group in W or, when W is a covalent bond, forms a bond with the ε-amino group of a Lys residue present in the A- or B-chain of the parent insulin.

In a further aspect, the substructure X of the side chain can be a group of the formula —CON(CH$_2$CH$_2$COOH)CH$_2$CO— that, via a bond from the underscored carbonyl carbon in X, forms an amide bond with an amino group in W or, when W is a covalent bond, forms a bond with the ε-amino group of a Lys residue present in the A- or B-chain of the parent insulin.

In a further aspect, the substructure X of the side chain can be a group of the formula —CON(CH$_2$COOH)CH$_2$CH$_2$CO— that, via a bond from the underscored carbonyl carbon in X, forms an amide bond with an amino group in W or, when W is a covalent bond, forms a bond with the ε-amino group of a Lys residue present in the A- or B-chain of the parent insulin.

The substructure Y of the side chain —W—X—Y—Z can be a group of the formula —(CH$_2$)$_m$— where m is an integer in the range of from 6 to 32, from 8 to 20, or from 12 to 20, or m is 11, 12, 13, 14, 15 or 16.

In another aspect, Y is a divalent hydrocarbon chain comprising 1, 2 or 3 —CH=CH— groups and a number of —CH$_2$— groups sufficient to give a total number of carbon atoms in the chain in the range of from 6 to 32, from 10 to 32, or from 12 to 20.

In one aspect, Y is a divalent hydrocarbon chain of the formula —(CH$_2$)$_v$C$_6$H$_4$(CH$_2$)$_w$— wherein v and w are integers or one of them is zero so that the sum of v and w is in the range of 6 to 30 or from 10 to 20.

In one aspect, the substructure Z of the side chain —W—X—Y—Z is —COOH provided that when W is a covalent bond and X is —CO—, then Z is different from —COOH.

In one aspect, Z is —CO-Asp.
In one aspect, Z is —CO-Glu.
In one aspect, Z is —CO-Gly.
In one aspect, Z is —CO-Ser.
In one aspect, Z is —CH(COOH)$_2$.
In one aspect, Z is —N(CH$_2$COOH)$_2$.
In one aspect, Z is —SO$_3$H.
In one aspect, Z is —PO$_3$H.

In one aspect of the invention the insulin derivative is having a formula:

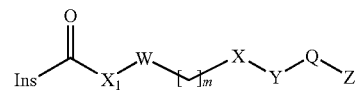

wherein Ins is a parent insulin moiety and —C(O)—X$_1$—W—[CH$_2$]$_m$—X—Y-Q-Z is a substituent and where the Ins is attached to the substituent via an amide bond between an ε-amino group of a Lys residue present in the A or B chain of Ins and a CO-group bound to X$_1$, W. [CH$_2$]$_m$, Y or Q in the substituent;

X$_1$ is
—(CH$_2$), where n is 1, 2, 3, 4, 5 or 6;
NR, where R is hydrogen or —(CH$_2$)$_p$—COOH; —(CH$_2$)$_p$—SO$_3$H; —(CH$_2$)$_p$—PO$_3$H$_2$; —(CH$_2$)$_p$—O—SO$_3$H$_2$; —(CH$_2$)$_p$—O—PO$_3$H$_2$; an aryl group substituted with 1 or 2-(CH$_2$)$_p$—O—COOH groups; —(CH$_2$)$_p$-tetrazol-5-yl, where p is an integer in the range of 1 to 6;
—(CR$_1$R$_2$)$_q$—NR—CO— where R$_1$ and R$_2$ can be H, —COOH, or OH, q is 1-6 and R is defined as above;
—((CR$_3$R$_4$)$_{q1}$—NR—CO)$_{2-4}$—, where R$_3$ and R$_4$ can be H, —COOH, or OH, q$_1$ is 1-6 and R is defined as above; or a bond W is arylene or heteroarylene, which may be substituted with one or two groups selected from the group consisting of —COOH, —SO$_3$H, and —PO$_3$H$_2$ and tetrazol-5-yl, or W is a bond;

m is 0, 1, 2, 3, 4, 5 or 6;
X is
—O—;

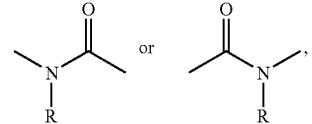

where R is defined as above; or
a bond;
Y is
—(CR$_1$R$_2$)$_q$—NR—CO—, where R$_1$ and R$_2$ can be H, —COOH, a bond or OH, q is 1-6; and R is defined as above;
NR where R is defined as above;
—((CR$_3$R$_4$)$_{q1}$—NR—CO)$_{2-4}$—, where R$_3$ and R$_4$ can be H, —COOH, or OH, q$_1$ is 1-6 and R is defined as above; or a bond;
Q is
—(CH$_2$)$_r$— where r is an integer from 4 to 22;

a divalent hydrocarbon chain comprising 1, 2 or 3 —CH=CH— groups and a number of —CH$_2$— groups sufficient to give a total number of carbon atoms in the chain in the range of 4 to 22; or a divalent chain of the formula

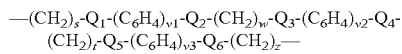

wherein $Q_1$-$Q_6$ independently of each other can be O; S or a bond; where s, w, t and z independently of each other are zero or an integer from 1 to 10 so that the sum of s, w, t and z is in the range from 4 to 22, and $v_1$, $v_2$, and $v_3$ independently of each other can be zero or 1, with the proviso that $Q_1$, $Q_2$, $Q_3$, $Q_4$, $Q_5$ and $Q_6$ may not form bonds to each other and if s, w, t and z are zero or 1, then no —CH$_2$— may be bound to 2 of the following atoms: O, S; and Z is:
—COOH;
—CO-Asp;
—CO-Glu;
—CO-Gly;
—CO-Ser;
—CH(COOH)$_2$;
—N(CH$_2$COOH)$_2$;
—SO$_3$H
—PO$_3$H$_2$;
O—SO$_3$H;
O—PO$_3$H$_2$;
-tetrazol-5-yl or
—O—W$_1$,
where W$_1$ is arylene or heteroarylene substituted with one or two groups selected from —COOH, —SO$_3$H, and —PO$_3$H$_2$ and tetrazol-5-yl;
and any Zn$^{2+}$ complex thereof.

In one aspect of the invention X$_1$ can be —(CH$_2$), where n is 1, 2, 3, 4, 5 or 6.

In one aspect of the invention X$_1$ can be NR, where R is hydrogen or —(CH$_2$)$_p$—COOH; —(CH$_2$)$_p$—SO$_3$H; —(CH$_2$)$_p$—PO$_3$H$_2$; —(CH$_2$)$_p$—O—SO$_3$H$_2$; —(CH$_2$)$_p$—O—PO$_3$H$_2$; an aryl group substituted with 1 or 2 —(CH$_2$)$_p$—O—COOH groups; —(CH$_2$)$_p$-tetrazol-5-yl, where p is an integer in the range of 1 to 6.

In one aspect X$_1$ can be —(CR$_1$R$_2$)$_q$—NR—CO—. For example X$_1$ can be —(CH$_2$)—(CHCOOH)—NH—CO— or —(CH$_2$)$_2$—(CHCOOH)—NH—CO—.

In one aspect X$_1$ can be —((CR$_3$R$_4$)$_{q'}$—NR—CO)$_{2-4}$— or X$_1$ can be a bond.

In one aspect W can be phenylene or W can be a 5-7 membered heterocyclic ring system comprising nitrogen, oxygen or sulphur. When W is a 5 membered heterocyclic ring it can comprise at least one oxygen.

In one aspect W is arylene, which may be substituted with —COOH. In one aspect W is a bond.

In one aspect X is —O—,

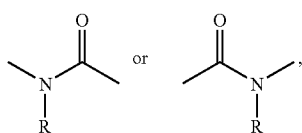

where R can be hydrogen or —(CH$_2$)$_p$—COOH. In one aspect p is 1 or 2.

In one aspect X is a bond.

In one aspect Y is —(CR$_1$R$_2$)$_q$—NR—CO—, where q is 1 and R$_1$ and R$_2$ are hydrogen. For example Y can be —CH$_2$—NH—CO— or —(CH$_2$)$_3$—(CHCOOH)—NH—CO—.

In one aspect Y is (CR$_3$R$_4$)$_q$, —NR—CO where R$_3$ and R$_4$ can be H, —COOH, or OH, q, is 1-6 and R is defined as above.

In one aspect Y is —((CR$_3$R$_4$)$_{q1}$—NR—CO)$_{2-4}$—, where R$_3$ and R$_4$ can be H, —COOH, or OH, q$_1$ is 1-6 and R is defined as above. In one aspect Y is a bond.

In one aspect Q is —(CH$_2$)$_r$, where r is an integer from 4 to 22, from 8 to 20 or from 10 to 18. For example r can be 12, 13, 14, 15, 16, 17 or 18.

In one aspect Q is a divalent chain comprising 1, 2 or 3 —CH=CH— groups and a number of —CH$_2$— groups sufficient to give a total number of carbon atoms in the chain in the range of 4 to 22.

In one aspect Q is a divalent chain of the formula:

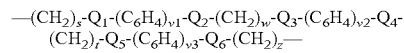

wherein $Q_1$-$Q_6$ independently of each other can be O; S or a bond; where s, w, t and z independently of each other are zero or an integer from 1 to 10 so that the sum of s, w, t and z is in the range from 4 to 22, and $v_1$, $v_2$, and $v_3$ independently of each other can be zero or 1.

In one aspect s is 1 or 2, 9, 10 or 11. In one aspect v$_1$ is 1 or 2. In one aspect $Q_1$, $Q_2$, $Q_5$ and $Q_6$ are all a bond. In one aspect $Q_1$ is S or O. In one aspect w is 2. In one v$_2$ is 1 and t is 1.

In one aspect Z is —COOH, —CO-Asp, —CO-Glu, —CO-Gly, —CO-Ser, —CH(COOH)$_2$, —N(CH$_2$COOH)$_2$, —SO$_3$H, —PO$_3$H$_2$, —O—SO$_3$H, —O—PO$_3$H$_2$ or -tetrazol-5-yl.

In one aspect Z is —O—W$_1$, where W$_1$ is arylene or heteroarylene substituted with one or two groups selected from —COOH, —SO$_3$H, and —PO$_3$H$_2$ and tetrazol-5-yl.

The insulin moiety—in the present text also referred to as the parent insulin—of the insulin derivative according to the invention can be an insulin analogue, which may contain only one lysine residue, which is not present at position B29 of the B-chain of the insulin analogue. This lysine residue may be in one of positions A8, A9, A10, A12, A14, A15, A17, A18, A21, A22, A23 or A24 in the A-chain of the parent insulin or to an ε-amino group of a Lys residue in the B-chain at position B1, B2, B3, B4, B20, B21 or B22 in the B-chain of the parent insulin.

The parent insulin can for example be human insulin or porcine insulin, wherein the Lys residue in position B29 is substituted and a Lys residue has been inserted in a position in the A-chain or B-chain, which position is not B29 of the B-chain.

In one aspect the amino acid residue at one of the positions A8, A9, A10, A12, A14, A15, A17, A18, A21, A22, A23 or A24 of the A-chain of the parent insulin is a Lys residue.

In one aspect the amino acid residue at one of the positions position B1, B2, B3, B4, B20, B21 or B22 of the B-chain of the parent insulin is a Lys residue.

In one group of parent insulin analogues, the amino acid residue at position B29 is Arg, Pro or Thr.

In one group of parent insulin analogues, the amino acid residue at position B1 and/or B30 has been deleted.

In one group of parent insulin analogues the amino acid residue at position B29 is Arg, Pro or Thr and the amino acid residue at one of the positions A8, A9, A10, A12, A14, A15, A17, A18, A21, A22, A23, A24, B1, B2, B3, B4, B20, B21 or B22 of the A or the B chain is Lys. A specific example from this group is LysA17 ArgB29 human insulin.

In one group of parent insulin analogues, the amino acid residues at position B30 has been deleted and the amino acid residue at position B29 can be any codable amino acid except Lys and the amino acid residue at one of the positions A8, A9, A10, A12, A14, A15, A17, A18, A21, A22, A23, A24, B1, B2, B3, B4, B20, B21 or B22 of the A- or the B-chain is Lys, provided that when Lys is at position B3, then B29 is not Glu. A specific example from this group of parent insulin analogues is LysA12 HisB29 desB30 human insulin.

In one group of parent insulin analogues, the amino acid residues at position B29 and B30 have been deleted and the amino acid residue at one of the positions A8, A9, A10, A12, A14, A15, A17, A18, A21, A22, A23, A24, B1, B2, B3, B4, B20, B21 or B22 of the A- or the B-chain is Lys. A specific example from this group of parent insulin analogues is LysA8 desB29 desB30 human insulin.

In one group of parent insulin analogues, the amino acid residue at position B26, B27, B28, B29 and B30 can be any codable amino acid except Lys or a deletion and the amino acid at one of the positions A8, A9, A10, A12, A14, A15, A17, A18, A21, A22, A23, A24, B1, B2, B3, B4, B20, B21 or B22 of the A- or the B-chain is Lys, provided that when Lys is at position B3, then B29 is not Glu. A specific example from this group of parent insulin analogues is LysB4 desB26 desB27 desB28 desB29 desB30 human insulin.

In one group of parent insulin analogues, the A-chain has been extended at the C-terminus with one, two or three amino acid residues, the positions of the extended amino acid residues being at position A22, A23 or A24. A Lys substitutes one of the amino acids at position A22, A23 or A24 of the A-chain. Any of the one or two remaining amino acid positions in the extension may be any codable amino acid residue except Lys. A specific example from this group of parent insulin analogues is LysA22 ArgB29 desB30 human insulin or GlyA22 LysA23 ArgB29 desB30 human insulin.

In one aspect of the invention the amino acid residue at position A21 of the parent insulin is Gly or Asn. The amino acid residue at position A21 of the parent insulin should be Gly, Ala or Gln when the amino acid residue at position A23 or A24 of the parent insulin is Lys.

In one aspect the amino acid residue at position B3 of the parent insulin is Lys or the amino acid residue at position B28 of the parent insulin is Asp.

Examples of parent insulin analogues are ArgB29 human insulin or ArgB29desB30 human insulin.

In a still further aspect the insulin derivative is selected from the group consisting of $N^{\epsilon A8}$-myristyl LysA8 ArgB29 desB30 human insulin, $N^{\epsilon A9}$-myristyl LysA9 ArgB29 desB30 human insulin, $N^{\epsilon A10}$-myristyl LysA10 ArgB29 desB30 human insulin, $N^{\epsilon A12}$-myristyl LysA12 ArgB29 desB30 human insulin, $N^{\epsilon A14}$-myristyl LysA14 ArgB29 desB30 human insulin $N^{\epsilon A15}$-myristyl LysA15 ArgB29 desB30 human insulin, $N^{\epsilon A17}$-myristyl LysA17 ArgB29 desB30 human insulin, $N^{\epsilon A18}$-myristyl LysA18 ArgB29 desB30 human insulin, $N^{\epsilon A21}$-myristyl LysA21 ArgB29 desB30 human insulin, $N^{\epsilon A22}$-myristyl LysA22 ArgB29 desB30 human insulin, $N^{\epsilon B1}$-myristyl LysB1 ArgB29 desB30 human insulin, $N^{\epsilon B2}$-myristyl LysB2 ArgB29 desB30 human insulin, $N^{\epsilon B3}$-myristyl LysB3 ArgB29 desB30 human insulin, $N^{\epsilon B4}$-myristyl LysB4 ArgB29 desB30 human insulin, $N^{\epsilon B20}$-myristyl LysB20 ArgB29 desB30 human insulin, $N^{\epsilon B21}$-myristyl LysB21 ArgB29 desB30 human insulin and $N^{\epsilon B22}$-myristyl LysB22 ArgB29 desB30 human insulin.

In a still further aspect the insulin derivative is selected from the group consisting of $N^{\epsilon A8}$-ω-carboxypentadecanoyl-γ-Glu LysA8 ArgB29 desB30 human insulin, $N^{\epsilon A9}$-ω-carboxypentadecanoyl-γ-Glu LysA9 ArgB29 desB30 human insulin, $N^{\epsilon A10}$-ω-carboxypentadecanoyl-γ-Glu LysA10 ArgB29 desB30 human insulin, $N^{\epsilon A12}$-ω-carboxypentadecanoyl-γ-Glu LysA12 ArgB29 desB30 human insulin, $N^{\epsilon A14}$-ω-carboxypentadecanoyl-γ-Glu LysA14 ArgB29 desB30 human insulin, $N^{\epsilon A15}$-ω-carboxypentadecanoyl-γ-Glu LysA15 ArgB29 desB30 human insulin, $N^{\epsilon A17}$-ω-carboxypentadecanoyl-γ-Glu LysA17 ArgB29 desB30 human insulin, $N^{\epsilon A18}$-ω-carboxypentadecanoyl-γ-Glu LysA18 ArgB29 desB30 human insulin, $N^{\epsilon A21}$-ω-carboxypentadecanoyl-γ-Glu LysA21 ArgB29 desB30 human insulin, $N^{\epsilon A22}$-ω-carboxypentadecanoyl-γ-Glu LysA22 ArgB29 desB30 human insulin, $N^{\epsilon B1}$-ω-carboxypentadecanoyl-γ-Glu LysB1 ArgB29 desB30 human insulin, $N^{\epsilon B2}$-ω-carboxypentadecanoyl-γ-Glu LysB2 ArgB29 desB30 human insulin, $N^{\epsilon B3}$-ω-carboxypentadecanoyl-γ-Glu LysB3 ArgB29 desB30 human insulin, $N^{\epsilon B4}$-ω-carboxypentadecanoyl-γ-Glu LysB4 ArgB29 desB30 human insulin, $N^{\epsilon B20}$-ω-carboxypentadecanoyl-γ-Glu LysB20 ArgB29 desB30 human insulin, $N^{\epsilon B21}$-ω-carboxypentadecanoyl-γ-Glu LysB21 ArgB29 desB30 human insulin and $N^{\epsilon B22}$-ω-carboxypentadecanoyl-γ-Glu LysB22 ArgB29 desB30 human insulin.

In a further aspect the insulin derivative is selected from the group consisting of $N^{\epsilon A22}$-ω-carboxypentadecanoyl-γ-Glu LysA22 GlyA21 ArgB29 desB30 human insulin, $N^{\epsilon A22}$-ω-carboxypentadecanoyl-γ-Glu LysA22 AlaA21 ArgB29 desB30 human insulin $N^{\epsilon A22}$-ω-carboxypentadecanoyl-γ-Glu LysA22 GlnA21 ArgB29 desB30 human insulin, $N^{\epsilon A22}$-ω-carboxypentadecanoyl-γ-Glu LysA23 GlyA21 GlyA22 ArgB29 desB30 human insulin, $N^{\epsilon A23}$-ω-carboxypentadecanoyl-γ-Glu LysA23 AlaA21 GlyA22 ArgB29 desB30 human insulin, $N^{\epsilon A23}$-ω-carboxypentadecanoyl-γ-Glu LysA23 GlnA21 GlyA22 ArgB29 desB30 human insulin, $N^{\epsilon A24}$-ω-carboxypentadecanoyl-γ-Glu LysA24 GlyA21 GlyA22 GlyA23 ArgB29 desB30 human insulin, $N^{\epsilon A24}$-ω-carboxypentadecanoyl-γ-Glu LysA24 AlaA21 GlyA22 GlyA23 ArgB29 desB30 human insulin, $N^{\epsilon A24}$-ω-carboxypentadecanoyl-γ-Glu LysA24 GlnA21 GlyA22 GlyA23 ArgB29 desB30 human insulin, $N^{\epsilon A22}$-ω-carboxyheptadecanoyl-γ-Glu LysA22 ArgB29 desB30 human insulin, $N^{\epsilon A23}$-ω-carboxyheptadecanoyl-γ-Glu LysA23 GlyA22 ArgB29 desB30 human insulin, $N^{\epsilon A23}$-ω-carboxyheptadecanoyl-γ-Glu LysA23 GlyA21 GlyA22 ArgB29 desB30 human insulin, $N^{\epsilon A23}$-ω-carboxyheptadecanoyl-γ-Glu LysA23 AlaA21 GlyA22 ArgB29 desB30 human insulin, $N^{\epsilon A23}$-ω-carboxyheptadecanoyl-γ-Glu LysA23 GlnA21 GlyA22 ArgB29 desB30 human insulin, $N^{\epsilon A24}$-ω-carboxyheptadecanoyl-γ-Glu LysA24 GlyA21 GlyA22 GlyA23 ArgB29 desB30 human insulin $N^{\epsilon A24}$-ω-carboxyheptadecanoyl-γ-Glu LysA24 AlaA21 GlyA22 GlyA23 ArgB29 desB30 human insulin and $N^{\epsilon A24}$-ω-carboxyheptadecanoyl-γ-Glu LysA24 GlnA21 GlyA22 GlyA23ArgB29 desB30 human insulin.

Insulin derivatives according to the invention may be provided in the form of essentially zinc free compounds or in the form of zinc complexes. When zinc complexes of an insulin derivative according to the invention are provided, about two zinc ions, about three zinc ions or about four zinc ions or even up to 12 zinc ions can be bound to 6 molecules of insulin derivative (hexamer). Solutions of zinc complexes of the insulin derivatives will contain mixtures of such species.

The zinc content in a pharmaceutical composition may be up to about 12 zinc ions per 6 molecules of insulin derivative. The upper limit for the zinc content is the content of zinc which would cause precipitation of the insulin and turning the solution into a suspension.

In one aspect of the invention the pharmaceutical composition comprises between about 4.3 and about 12 zinc ions per 6 molecules of insulin derivative or between about 4.5 and about 12 zinc ions per 6 molecules of insulin derivative. In a further aspect of the invention the pharmaceutical composition comprises between above 5 and about 11.4 zinc ions per 6 molecules of insulin derivative or between about 5.5 and about 10 zinc ions per 6 molecules of insulin derivative.

The invention further comprises a method for producing a pharmaceutical composition comprising an insulin derivative wherein more than about 4 zinc ions per 6 molecules of insulin derivative are added to the composition.

In one aspect of the invention the method comprises adding up to about 12 zinc ions per 6 molecules of insulin derivative to the composition.

In one aspect of the invention the method comprises adding between about 4.3 and about 12 zinc ions per 6 molecules of insulin derivative to the composition.

In a further aspect of the invention between about 4.5 and about 12 zinc ions per 6 molecules of insulin derivative are added to the composition, for example about 5 and about 11.4 zinc ions per 6 molecules of insulin derivative are added to the composition or between about 5.5 and about 10 zinc ions per 6 molecules of insulin derivative are added to the composition.

One aspect of the invention concerns a method for producing a pharmaceutical composition. The method comprises adding zinc to the composition before the addition of a preservative. In one aspect of the invention between about 4.5 and about 12 zinc ions per 6 molecules of insulin derivative are added to the composition before the addition of a preservative or for example about 5 and about 11.4 zinc ions per 6 molecules of insulin derivative are added to the composition before the addition of a preservative or for example between about 5.5 and about 10 zinc ions per 6 molecules of insulin derivative are added to the composition before the addition of a preservative.

In one aspect of the invention the method comprises adding up to about 12 zinc ions to the composition after addition of a preservative.

In one aspect of the invention at least 0.5 zinc ion per 6 molecules of insulin derivative is added to the composition after addition of a preservative or at least 1 zinc ion per 6 molecules of insulin derivative is added to the composition after addition of a preservative.

In a further aspect of the invention more than about 2, 3, 4, 5, or 6 zinc ions per 6 molecules of insulin derivative are added to the composition after the addition of a preservative In a further aspect of the invention between about 4.5 and about 12 zinc ions per 6 molecules of insulin derivative are added to the composition after the addition of a preservative or between about 5.5 and about 10 zinc ions per 6 molecules of insulin derivative are added to the composition after the addition of a preservative.

In one aspect of the invention the method comprises adding part of the zinc before addition of a preservative and part of the zinc after addition of a preservative.

In one aspect the method comprises adding at least 1 zinc ion per 6 molecules of insulin derivative before addition of a preservative and adding at least 1 zinc ion per 6 molecules of insulin derivative after addition of a preservative.

In another aspect of the invention the method comprises adding at least 1, 2, 3, 4, 5 or 6 zinc ion per 6 molecules of insulin derivative before addition of a preservative and adding at least 2, 3, 4, 5 or 6 zinc ions per 6 molecules of insulin derivative after addition of a preservative.

In one aspect of the invention the number of zinc ions added before addition of a preservative is at least 3 zinc ion per 6 molecules of insulin derivative and the number of zinc ions added after addition of a preservative are at least 3 zinc ions per 6 molecules of insulin derivative.

In one aspect of the invention the preservative added is phenol and/or m-cresol.

In a further aspect the invention is related to a pharmaceutical composition comprising a therapeutically effective amount of an insulin derivative or a zinc complex of the insulin derivative according to the invention together with a pharmaceutically acceptable carrier can be provided for the treatment of type 1 diabetes, type 2 diabetes and other states that cause hyperglycaemia in patients in need of such a treatment.

An insulin derivative or a pharmaceutical composition comprising the insulin derivative or a zinc complex of the insulin derivative according to the invention can be used for the manufacture of a pharmaceutical composition for the use in the treatment of type 1 diabetes, type 2 diabetes and other states that cause hyperglycaemia.

In a further aspect of the invention, there is provided a pharmaceutical composition for treating type 1 diabetes, type 2 diabetes and other states that cause hyperglycaemia in a patient in need of such a treatment, comprising a therapeutically effective amount of an insulin derivative or a zinc complex of the insulin derivative according to the invention in mixture with an insulin or an insulin analogue which has a rapid onset of action, together with pharmaceutically acceptable carriers and additives.

In one aspect the invention provides a pharmaceutical composition being a mixture of an insulin derivative or a zinc complex of the insulin derivative according to the invention and human insulin or a rapid acting insulin analogue selected group consisting of AspB28 human insulin; LysB28ProB29 human insulin and LysB3GluB29 human insulin.

In a further aspect the invention is related to a pulmonary application for treating type 1 diabetes, type 2 diabetes and other states that cause hyperglycaemia in a patient in need of such a treatment, comprising a therapeutically effective amount of an insulin derivative or a zinc complex of the insulin derivative according to the invention optionally in mixture with an insulin or an insulin analogue which has a rapid onset of action, together with pharmaceutically acceptable carriers and additives.

The insulin derivative according to the invention and the rapid acting insulin analogue can be mixed in a ratio from about 90/10%; about 70/30% or about 50/50%.

In a further aspect of the invention, there is provided a method of treating type 1 diabetes, type 2 diabetes and other states that cause hyperglycaemia in a patient in need of such a treatment, comprising administering to the patient a therapeutically effective amount of an insulin derivative according to the invention together with a pharmaceutically acceptable carrier and pharmaceutical acceptable additives.

In a further aspect of the invention, there is provided a method for the manufacture of a pharmaceutical composition for the use in the treatment of type 1 diabetes, type 2 diabetes and other states that cause hyperglycaemia, the composition comprising the insulin derivative according to the invention together with a pharmaceutically acceptable carrier and pharmaceutical acceptable additives.

In a further aspect of the invention, there is provided a method of treating type 1 diabetes, type 2 diabetes and other states that cause hyperglycaemia in a patient in need of such a treatment, comprising administering to the patient a therapeutically effective amount of an insulin derivative according to the invention in mixture with an insulin or an insulin analogue which has a rapid onset of action, together with a pharmaceutically acceptable carrier and pharmaceutical acceptable additives.

In a further aspect of the invention, there is provided a method for the manufacture of a pharmaceutical composition for the use in the treatment of type 1 diabetes, type 2 diabetes and other states that cause hyperglycaemia, the composition comprising an insulin derivative according to the invention in mixture with an insulin or an insulin analogue which has a rapid onset of action, together with a pharmaceutically acceptable carrier and pharmaceutical acceptable additives.

In another aspect, the invention relates to a pharmaceutical composition comprising an insulin derivative according to the invention which is soluble at physiological pH values.

In another aspect, the invention relates to a pharmaceutical composition comprising an insulin derivative according to the invention which is soluble at pH values in the interval from about 6.5 to about 8.5.

In another aspect, the invention relates to a pharmaceutical composition with a prolonged profile of action which comprises an insulin derivative according to the invention.

In another aspect, the invention relates to a pharmaceutical composition which is a solution containing from about 120 nmol/ml to about 2400 nmol/ml, from about 400 nmol/ml to about 2400 nmol/ml, from about 400 nmol/ml to about 1200 nmol/ml, from about 600 nmol/ml to about 2400 nmol/ml, or from about 600 nmol/ml to about 1200 nmol/ml of an insulin derivative according to the invention or of a mixture of the insulin derivative according to the invention with a rapid acting insulin analogue.

The starting product for the acylation, the parent insulin or insulin analogue or a precursor thereof can be produced by either well-know peptide synthesis or by well known recombinant production in suitable transformed microorganisms. Thus the insulin starting product can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the parent insulin may suitably be of genomic or cDNA origin, for instance obtained by preparing a genomic or cDNA library and screening for DNA sequences coding for all or part of the polypeptide by hybridisation using synthetic oligonucleotide probes in accordance with standard techniques (see, for example, Sambrook, J. Fritsch, E F and Maniatis, T. *Molecular Cloning: A Laboratory Manual*, Cold Spring Harbor Laboratory Press, New York, 1989). The DNA sequence encoding the parent insulin may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is for example an expression vector in which the DNA sequence encoding the parent insulin is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the parent insulin in a variety of host cells are well known in the art, cf. for instance Sambrook et al., supra.

The DNA sequence encoding the parent insulin may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracycline chloramphenicol, neomycin, hygromycin or methotrexate.

To direct a peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the parent insulin, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

The parent insulin molecule is then converted into the insulin derivatives of the invention by introducing of the relevant side chain in either the B1 position or in the chosen Lys position in the B-chain. The side chain can be introduced by any convenient method and many methods are disclosed in the prior art for acylation of an amino group. More details will appear from the following examples.

Pharmaceutical Compositions

The insulin derivatives of this invention of the claimed formula can, for example, be administered subcutaneously, orally, or pulmonary.

For subcutaneous administration, the compounds of the formula are formulated analogously with the formulation of known insulins. Furthermore, for subcutaneous administration, the compounds of the formula are administered analogously with the administration of known insulins and, generally, the physicians are familiar with this procedure.

The insulin derivatives of this invention may be administered by inhalation in a dose effective manner to increase circulating insulin levels and/or to lower circulating glucose levels. Such administration can be effective for treating disorders such as diabetes or hyperglycemia. Achieving effective doses of insulin requires administration of an inhaled dose of insulin derivative of this invention of more than about 0.5 µg/kg to about 50 µg/kg. A therapeutically effective amount can be determined by a knowledgeable practitioner, who will take into account factors including insulin level, blood glucose levels, the physical condition of the patient, the patient's pulmonary status, or the like.

According to the invention, insulin derivative of this invention may be delivered by inhalation to achieve rapid absorption thereof. Administration by inhalation can result in pharmacokinetics comparable to subcutaneous administration of insulins. Inhalation of a insulin derivative of this invention leads to a rapid rise in the level of circulating insulin followed by a rapid fall in blood glucose levels. Different inhalation devices typically provide similar pharmacokinetics when similar particle sizes and similar levels of lung deposition are compared.

According to the invention, insulin derivative of this invention may be delivered by any of a variety of inhalation devices known in the art for administration of a therapeutic agent by inhalation. These devices include metered dose inhalers, nebulizers, dry powder generators, sprayers, and the like. Insulin derivative of this invention is delivered by a dry powder inhaler or a sprayer. There are a several desirable features of an inhalation device for administering insulin derivative of this invention. For example, delivery by the inhalation device is advantageously reliable, reproducible, and accurate. The inhalation device should deliver small particles, for example, less than about 10 µm, for example about 1-5 µm, for good respirability. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

As those skilled in the art will recognize, the formulation of insulin derivative of this invention, the quantity of the formulation delivered, and the duration of administration of a single dose depend on the type of inhalation device employed. For some aerosol delivery systems, such as nebulizers, the frequency of administration and length of time for which the system is activated will depend mainly on the concentration of insulin conjugate in the aerosol. For example, shorter periods of administration can be used at higher concentrations of insulin conjugate in the nebulizer solution. Devices such as metered dose inhalers can produce higher aerosol concentrations, and can be operated for shorter periods to deliver the desired amount of insulin conjugate. Devices such as powder inhalers deliver active agent until a given charge of agent is expelled from the device. In this type of inhaler, the amount of insulin derivative of this invention in a given quantity of the powder determines the dose delivered in a single administration.

The particle size of insulin derivative of this invention in the formulation delivered by the inhalation device is critical with respect to the ability of insulin to make it into the lungs, and into the lower airways or alveoli. The insulin derivative of this invention can be formulated so that at least about 10% of the insulin conjugate delivered is deposited in the lung, for example about 10 to about 20%, or more. It is known that the maximum efficiency of pulmonary deposition for mouth breathing humans is obtained with particle sizes of about 2 μm to about 3 μm. When particle sizes are above about 5 μm pulmonary deposition decreases substantially. Particle sizes below about 1 μm cause pulmonary deposition to decrease, and it becomes difficult to deliver particles with sufficient mass to be therapeutically effective. Thus, particles of the insulin derivative delivered by inhalation have a particle size less than about 10 μm, for example in the range of about 1 μm to about 5 μm. The formulation of the insulin derivative is selected to yield the desired particle size in the chosen inhalation device.

Advantageously for administration as a dry powder, an insulin derivative of this invention is prepared in a particulate form with a particle size of less than about 10 μm, for example about 1 to about 5 μm. The particle size is effective for delivery to the alveoli of the patient's lung. The dry powder is largely composed of particles produced so that a majority of the particles have a size in the desired range. Advantageously, at least about 50% of the dry powder is made of particles having a diameter less than about 10 μm. Such formulations can be achieved by spray drying, milling, or critical point condensation of a solution containing insulin conjugate and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Formulations of insulin derivatives of this invention for administration from a dry powder inhaler typically include a finely divided dry powder containing the derivative, but the powder can also include a bulking agent, carrier, excipient, another additive, or the like. Additives can be included in a dry powder formulation of insulin conjugate, for example, to dilute the powder as required for delivery from the particular powder inhaler, to facilitate processing of the formulation, to provide advantageous powder properties to the formulation, to facilitate dispersion of the powder from the inhalation device, to stabilize the formulation (for example, antioxidants or buffers), to provide taste to the formulation, or the like. Advantageously, the additive does not adversely affect the patient's airways. The insulin derivative can be mixed with an additive at a molecular level or the solid formulation can include particles of the insulin conjugate mixed with or coated on particles of the additive. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as insulin analogue protein can also be included in the formulation.

A spray including the insulin derivatives of this invention can be produced by forcing a suspension or solution of insulin conjugate through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of insulin conjugate delivered by a sprayer have a particle size less than about 10 μm, for example in the range of about 1 μm to about 5 μm.

Formulations of insulin derivatives of this invention suitable for use with a sprayer will typically include the insulin derivative in an aqueous solution at a concentration of about 1 mg to about 20 mg of insulin conjugate per ml of solution. The formulation can include agents such as an excipient, a buffer, an isotonicity agent, a preservative, a surfactant, and, for example zinc. The formulation can also include an excipient or agent for stabilization of the insulin derivative, such as a buffer, a reducing agent, a bulk protein, or a carbohydrate. Bulk proteins useful in formulating insulin conjugates include albumin, protamine, or the like. Typical carbohydrates useful in formulating insulin conjugates include sucrose, mannitol, lactose, trehalose, glucose, or the like. The insulin derivative formulation can also include a surfactant, which can reduce or prevent surface-induced aggregation of the insulin conjugate caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation.

Pharmaceutical compositions containing an insulin derivative according to the present invention may also be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. Further options are to administer the insulin nasally or pulmonally, for example in compositions, powders or liquids, specifically designed for the purpose.

Injectable compositions of the insulin derivatives of the invention can be prepared using the conventional techniques of the pharmaceutical industry which involve dissolving and mixing the ingredients as appropriate to give the desired end product. Thus, according to one procedure, an insulin derivative according to the invention is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

In a further aspect of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative aspect of the invention.

In a further aspect of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine, 3-(4-chlorophenoxy)propane-1,2-diol or mixtures thereof. In a further aspect of the invention the preservative is present in a concentration from 0.1 mg/ml to 20 mg/ml. In a further aspect of the invention the preservative is present in a concentration from 0.1 mg/ml to 5 mg/ml. In a further aspect of the invention the preservative is present in a concentration from 5 mg/ml to 10 mg/ml. In a further aspect of the invention the preservative is present in a concentration from 10 mg/ml to 20 mg/ml. Each one of these specific preservatives constitutes an alternative aspect of the invention. The use of a preservative in pharmaceutical compositions is well-known to the skilled person. For convenience reference is made to Remington: *The Science and Practice of Pharmacy,* $19^{th}$ edition, 1995.

In a further aspect of the invention the formulation further comprises an isotonic agent which may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one aspect the sugar additive is sucrose. Sugar alcohol is defined as a C4-C8 hydrocarbon having at least one—OH group and includes, for example, mannitol, sorbitol, inositol, galactitol, dulcitol, xylitol, and arabitol. In one aspect the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one aspect, the sugar or sugar alcohol concentration is between about 1 mg/ml and about 150 mg/ml. In a further aspect of the invention the isotonic agent is present in a concentration from 1 mg/ml to 50 mg/ml. In a further aspect of the invention the isotonic agent is present in a concentration from 1 mg/ml to 7 mg/ml. In a further aspect of the invention the isotonic agent is present in a concentration from 8 mg/ml to 24 mg/ml. In a further aspect of the invention the isotonic agent is present in a concentration from 25 mg/ml to 50 mg/ml. Each one of these specific isotonic agents constitutes an alternative aspect of the invention. The use of an isotonic agent in pharmaceutical compositions is well-known to the skilled person. For convenience reference is made to Remington: *The Science and Practice of Pharmacy,* $19^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

A composition for nasal administration of an insulin derivative according to the present invention may, for example, be prepared as described in European Patent No. 272097 (to Novo Nordisk A/S).

Compositions containing insulin derivatives of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the insulin derivative of this invention be determined for each individual patient by those skilled in the art in a similar way as for known insulin compositions.

Where expedient, the insulin derivatives of this invention may be used in mixture with other types of insulin, e.g. insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention will be summarized in the following paragraphs:

1. An insulin derivative comprising a parent insulin and a substituent, wherein the substituent is attached either to an ε-amino group of a Lys residue present in the A-chain of the parent insulin at position A8, A9, A10, A12, A14, A15, A17, A18, A21, A22, A23 or A24 or to an ε-amino group of a Lys residue in the B-chain of the parent insulin at position B1, B2, B3, B4, B20, B21 or B22 provided that when B3 is Lys, then B29 is not Glu.

2. Insulin derivative according to paragraph 1, wherein the substituent is attached to the ε-amino group of the Lys residue present at position A8 in the A-chain of the parent insulin.

3. Insulin derivative according to paragraph 1, wherein the substituent is attached to the ε-amino group of the Lys residue present at position A9 in the A-chain of the parent insulin.

4. Insulin derivative according to paragraph 1, wherein the substituent is attached to the ε-amino group of the Lys residue present at position A14 in the A-chain of the parent insulin.

5. Insulin derivative according to paragraph 1, wherein the substituent is attached to the ε-amino group of the Lys residue present at position A18 in the A-chain of the parent insulin.

6. Insulin derivative according to paragraph 1, wherein the substituent is attached to the ε-amino group of the Lys residue present at position A21 in the A-chain of the parent insulin.

7. Insulin derivative according to paragraph 1, wherein the substituent is attached to the ε-amino group of the Lys residue present at position A22 in the A-chain of the parent insulin.

8. Insulin derivative according to paragraph 1, wherein the substituent is attached to the ε-amino group of the Lys residue present at position A23 in the A-chain of the parent insulin.

9. Insulin derivative according to paragraph 1, wherein the substituent is attached to the ε-amino group of the Lys residue present at position A24 in the A-chain of the parent insulin.

10. Insulin derivative according to paragraph 1-9, wherein the substituent is a lipophilic group containing from 4 to 40 carbon atoms.

11. Insulin derivative according to paragraphs 1-10, wherein the substituent comprises an acyl group having from 6 to 40 carbon atoms.

12. Insulin derivative according to paragraphs 11, wherein the substituent comprises an acyl group having from 12 to 36 carbon atoms.

13. Insulin derivative according to paragraphs 1-10, wherein the acyl group is $CH_3$—$(CH_2)_n$—CO—, where $4 \leq n \leq 38$.

14. An insulin derivative according to paragraphs 1-10, wherein the acyl group is (COOH)—$(CH_2)_n$—CO—, where $4 \leq n \leq 38$.

15. An insulin derivative according to paragraphs 1-10, wherein the acyl group is ($NH_2$—CO)—$(CH_2)_n$—CO—, where $4 \leq n \leq 38$.

16. An insulin derivative according to paragraphs 1-10, wherein the acyl group is HO—$(CH_2)_n$—CO—, where $4 \leq n \leq 38$.

17. Insulin derivative according to paragraphs 13-16, where $6 \leq n \leq 36$

18. Insulin derivative according to paragraphs 13-16, where $8 \leq n \leq 34$

19. Insulin derivative according to paragraphs 13-16, where $12 \leq n \leq 32$

20. Insulin derivative according to paragraphs 13-16, where $12 \leq n \leq 28$

21. An insulin derivative according to paragraphs 1-12, wherein the acyl group is 5-α lithocholic acid or 5-β lithocholic acid.

22. An insulin derivative according to paragraphs 1-12, wherein the acyl group is 5-α or 5-β isomers of cholic acid, hyocholic acid, deoxycholic acid, chenodeoxycholic acid, ursodeoxycholic acid, hyodeoxycholic acid or cholanic acid.

23. An insulin derivative according to paragraphs 1-12, wherein the acyl group is a 5-α or 5-β isomer of dehydrolithocholic acid.

24. An insulin derivative according to paragraphs 1-12, wherein the acyl group is fusidic acid, a fusidic acid derivative or glycyrrhetinic acid.

25. An insulin derivative according to paragraph 1-9 where the substituent is of general formula:

—W—X—Y—Z wherein W is:

an α-amino acid residue having a carboxylic acid group in the side chain which residue forms, with one of its carboxylic acid groups, an amide group with the ε-amino group of a Lys residue present in the A- or the B-chain of the parent insulin; or a chain composed of two, three or four α-amino acid residues linked together via amide bonds, which chain, via an amide bond, is linked to the ε-amino group of a Lys residue present in the A- or the B-chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or a covalent bond from X to the ε-amino group of a Lys residue present in the A- or the B-chain of the parent insulin;
X is:
—CO—;
—CH(COOH)CO—;
—CON(CH$_2$$\overline{C}$OOH)CH$_2$CO—;
—CON(CH$_2$COOH)CH$_2$$\overline{C}$ON(CH$_2$COOH)CH$_2$$\underline{C}$O—;
—CON(CH$_2$CH$_2$COOH)CH$_2$CH$_2$CO—;
—CON(CH$_2$CH$_2$COOH)CH$_2$CH$_2$$\overline{C}$ON(CH$_2$CH$_2$COOH)CH$_2$CH$_2$CO—;
—CO$\overline{N}$HCH(COOH)(CH$_2$)$_4$NHCO—;
—CON(CH$_2$CH$_2$COOH)CH$_2$$\underline{CO}$—; or
—CON(CH$_2$COOH)CH$_2$CH$_2$$\overline{C}$O—.
Provided that
a) when W is an amino acid residue or a chain of amino acid residues, the underscored carbonyl carbon in X forms an amide bond with an amino group in W, or
b) when W is a covalent bond, the underscored carbonyl carbon in X forms an amide bond with the ε-amino group of a Lys residue present in the A- or the B-chain of the parent insulin;
Y is:
—(CH$_2$)$_m$— where m is an integer in the range of 6 to 32;
a divalent hydrocarbon chain comprising 1, 2 or 3 —CH=CH— groups and a number of —CH$_2$— groups sufficient to give a total number of carbon atoms in the chain in the range of 10 to 32;
a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and
Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H;
and any Zn$^{2+}$ complexes thereof.

26. Insulin derivative according to paragraph 25, wherein W is an α-amino acid residue having a carboxylic acid group in the side chain which residue forms, with one of its carboxylic acid groups, an amide group with the ε-amino group of a Lys residue present in the A- or the B-chain of the parent insulin.

27. An insulin derivative according to any of paragraphs 26-27, wherein W is an α-amino acid residue having from 4 to 10 carbon atoms.

28. An insulin derivative according to paragraphs 25-27, wherein W is selected from the group consisting of α-Asp, G-Asp, α-Glu, γ-Glu, α-hGlu and 6-hGlu.

29. An insulin derivative according to paragraph 25, wherein W is a chain composed of two α-amino acid residues of which one has from 4 to 10 carbon atoms and a free carboxylic acid group while the other has from 2 to 11 carbon atoms but no free carboxylic acid group.

30. An insulin derivative according to paragraph 25 and 29 wherein W is selected from the group consisting of α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-b-hGlu.

31. An insulin derivative according to paragraph 25, wherein W is a chain composed of two α-amino acid residues, independently having from 4 to 10 carbon atoms, and both having a free carboxylic acid group.

32. An insulin derivative according to paragraph 25 and 31, wherein W is selected from the group consisting of α-Asp-α-Asp; α-Asp-α-Glu; α-Asp-α-hGlu; α-Asp-β-Asp; α-Asp-γ-Glu; α-Asp-b-hGlu; β-Asp-α-Asp; β-Asp-α-Glu; β-Asp-α-hGlu; β-Asp-β-Asp; β-Asp-γ-Glu; β-Asp-β-hGlu; α-Glu-α-Asp; α-Glu-α-Glu; α-Glu-α-hGlu; α-Glu-β-Asp; α-Glu-γ-Glu; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-β-Asp; α-hGlu-γ-Glu; α-hGlu-δ-hGlu; δ-hGlu-α-Asp; δ-hGlu-α-Glu; δ-hGlu-α-hGlu; δ-hGlu-β-Asp; 6-hGlu-γ-Glu; and δ-hGlu-δ-hGlu.

33. An insulin derivative according to paragraph 25, wherein W is a covalent bond.

34. An insulin derivative according to any of the paragraphs 25-33, wherein X is —CO— or —COCH(COOH)CO—.

35. An insulin derivative according to paragraphs 25-33, wherein X is
—CON(CH$_2$COOH)CH$_2$$\ddot{C}$O—;
—CON(CH$_2$COOH)CH$_2$CON(CH$_2$COOH)CH$_2$$\underline{C}$O—;
—CON(CH$_2$CH$_2$COOH)CH$_2$CH$_2$CO—;
—CON(CH$_2$CH$_2$COOH)CH$_2$CH$_2$CON(CH$_2$CH$_2$COOH)CH$_2$CH$_2$CO—;
—CO$\overline{N}$(CH$_2$CH$_2$COOH)CH$_2$CO—; or
—CON(CH$_2$COOH)CH$_2$CH$_2$$\ddot{C}$O—.

36. An insulin derivative according to any of paragraphs 25-35, wherein Y is —(CH$_2$)$_m$— where m is an integer in the range of from 6 to 32.

37. An insulin derivative according to paragraph 36 wherein m is in the range from 8-20.

38. An insulin derivative according to paragraphs 36-37, wherein m is 11, 12, 13, 14, or 16.

39. Insulin derivative according to any one of paragraphs 25-38, wherein Z is —COOH.

40. Insulin derivative according to any one of paragraphs 25-38, wherein Z is —CO-Asp.

41. Insulin derivative according to any one of paragraphs 25-38, wherein Z is —CO-Glu.

42. Insulin derivative according to any one of paragraphs 25-38, wherein Z is —CO-Gly.

43. Insulin derivative according to any one of paragraphs 25-38, wherein Z is —CO-Sar.

44. An insulin derivative according to any one of the paragraphs 25-38, wherein Z is —CH(COOH)$_2$.

45. An insulin derivative according to any one of the paragraphs 25-38, wherein Z is —N(CH$_2$COOH)$_2$.

46. An insulin derivative according to any one of the paragraphs 25-38, wherein Z is —SO$_3$H.

47. An insulin derivative according to any one of the paragraphs 25-38, wherein Z is —PO$_3$H.

48. Insulin derivative according to paragraph 1-9 having a formula $$\text{Ins} \diagdown \underset{\text{O}}{\text{C}} \diagdown X_1 \diagdown W \diagdown [\quad]_m \diagdown X \diagdown Y \diagdown Q \diagdown Z$$

wherein Ins is a parent insulin moiety and —C(O)—$X_1$—W—$[CH_2]_m$—X—Y-Q-Z is a substituent and where the Ins is attached to the substituent via an amide bond between an ε-amino group of a Lys residue present in the A or B chain of Ins and a CO-group bound to $X_1$, W, $[CH_2]_m$, Y or Q in the substituent;

$X_1$ is
—($CH_2$), where n is 1, 2, 3, 4, 5 or 6;
NR, where R is hydrogen or —($CH_2$)$_p$—COOH; —($CH_2$)$_p$—$SO_3H$; —($CH_2$)$_p$—$PO_3H_2$; —($CH_2$)$_p$—O—$SO_3H_2$; —($CH_2$)$_p$—O—$PO_3H_2$; an aryl group substituted with 1 or 2-($CH_2$)$_p$—O—COOH groups; —($CH_2$)$_p$-tetrazol-5-yl, where p is an integer in the range of 1 to 6;
—($CR_1R_2$)$_q$—NR—CO—, where $R_1$ and $R_2$ can be H, —COOH, or OH, q is 1-6 and R is defined as above;
—(($CR_3R_4$)$_{q1}$—NR—CO)$_{24}$—, where $R_3$ and $R_4$ can be H, —COOH, or OH, $q_1$ is 1-6 and R is defined as above; or
a bond W is arylene or heteroarylene, which may be substituted with one or two groups selected from the group consisting of —COOH, —$SO_3H$, and —$PO_3H_2$ and tetrazol-5-yl, or W is a bond;

m is 0, 1, 2, 3, 4, 5 or 6;
X is
—O—;

where R is defined as above; or
a bond;
Y is
—($CR_1R_2$)$_q$—NR—CO—, where $R_1$ and $R_2$ can be H, —COOH, a bond or OH, q is 1-6; and R is defined as above;
NR where R is defined as above;
—(($CR_3R_4$)$_{q1}$—NR—CO)$_{2-4}$—, where $R_3$ and $R_4$ can be H, —COOH, or OH, $q_1$ is 1-6 and R is defined as above; or
a bond;
Q is
—($CH_2$)$_r$— where r is an integer from 4 to 22;
a divalent hydrocarbon chain comprising 1, 2 or 3 —CH=CH— groups and a number of —$CH_2$— groups sufficient to give a total number of carbon atoms in the chain in the range of 4 to 22; or
a divalent chain of the formula —($CH_2$)$_s$-$Q_1$-($C_6H_4$)$_{v1}$-$Q_2$-($CH_2$)$_w$-$Q_3$-($C_6H_4$)$_{v2}$-$Q_4$-($CH_2$)$_t$-$Q_5$-($C_6H_4$)$_{v3}$-$Q_6$-($CH_2$)$_z$— wherein $Q_1$-$Q_6$ independently of each other can be O; S or a bond; where s, w, t and z independently of each other are zero or an integer from 1 to 10 so that the sum of s, w, t and z is in the range from 4 to 22, and $v_1$, $v_2$, and $v_3$ independently of each other can be zero or 1, with the proviso that $Q_1$, $Q_2$, $Q_3$, $Q_4$, $Q_5$ and $Q_6$ may not form bonds to each other and if s, w, t and z are zero or 1, then no —$CH_2$— may be bound to 2 of the following atoms: O, S; and Z is:
—COOH;
—CO-Asp;
—CO-Glu;
—CO-Gly;
—CO-Sar;
—CH(COOH)$_2$;
—N($CH_2$COOH)$_2$;
—$SO_3H$
—$PO_3H_2$;
O—$SO_3H$;
O—$PO_3H_2$;
-tetrazol-5-yl or
—O—$W_1$,
where $W_1$ is arylene or heteroarylene substituted with one or two groups selected from —COOH, —$SO_3H$, and —$PO_3H_2$ and tetrazol-5-yl;
and any $Zn^{2+}$ complex thereof.

49. Insulin derivative according to paragraph 48, wherein $X_1$ is —($CH_2$), where n is 1, 2, 3, 4, 5 or 6.

50. Insulin derivative according to paragraph 48, wherein $X_1$ is NR, where R is hydrogen or —($CH_2$)$_p$—COOH; —($CH_2$)$_p$—$SO_3H$; —($CH_2$)$_p$—$PO_3H_2$; —($CH_2$)$_p$—O—$SO_3H_2$; —($CH_2$)$_p$—O—$PO_3H_2$; an aryl group substituted with 1 or 2-($CH_2$)$_p$—O—COOH groups; —($CH_2$)$_p$-tetrazol-5-yl, where p is an integer in the range of 1 to 6;

51. Insulin derivative according to paragraph 48, wherein $X_1$ is —($CR_1R_2$)$_q$—NR—CO—.

52. Insulin derivative according to paragraph 51, wherein $X_1$ is —($CH_2$)—(CHCOOH)—NH—CO—.

53. Insulin derivative according to paragraph 51, wherein $X_1$ is —($CH_2$)$_2$—(CHCOOH)—NH—CO—.

54. Insulin derivative according to paragraph 48, wherein $X_1$ is —(($CR_3R_4$)$_{q'}$—NR—CO)$_{2-4}$—.

55. Insulin derivative according to paragraph 48, wherein $X_1$ is a bond.

56. An insulin derivative according to any of paragraphs 48-56, wherein W is phenylene.

57. An insulin derivative according to paragraph 48-56, wherein W is a 5-7 membered heterocyclic ring system comprising nitrogen, oxygen or sulphur.

58. An insulin derivative according to any of paragraphs 57, wherein W is a 5 membered heterocyclic ring system comprising at least one oxygen.

59. Insulin derivative according to paragraph 48-55, wherein W is arylene.

60. Insulin derivative according to paragraph 59, wherein W is arylene substituted with —COOH 61. An insulin derivative according to any of paragraphs 48-55, wherein W is a bond.

62. Insulin derivative according to any of the paragraphs 48-61, where X is —O—.

63. Insulin derivative according to any of the paragraphs 48-61, where X is:

64. Insulin derivative according to any of the paragraphs 48-61, where X is:

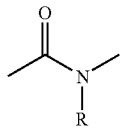

65. Insulin derivative according to paragraphs 63-64, where R is hydrogen.
66. Insulin derivative according to paragraphs 63-64, where R is —(CH$_2$)$_p$—COOH.
67. Insulin derivative according to paragraph 66, wherein p is 1.
68. Insulin derivative according to paragraph 66, wherein p is 2.
69. Insulin derivative according to paragraphs 48-61, where X is a bond
70. Insulin derivative according to any of paragraphs 48-69, wherein Y is —(CR$_1$R$_2$)$_q$—NR—CO—.
71. Insulin derivative according to paragraph 70, wherein Y is —CH$_2$—NH—CO—.
72. Insulin derivative according to paragraph 70, wherein Y is —(CH$_2$)$_3$—(CHCOOH)—NH—CO—.
73. Insulin derivative according to any of paragraphs 48-69, wherein Y is (CR$_3$R$_4$)$_{q1}$—NR—CO— where R$_3$ and R$_4$ can be H, —COOH, or OH, q$_1$ is 1-6 and R is defined as above.
74. Insulin derivative according to any of paragraphs 48-69, wherein Y is —((CR$_3$R$_4$)$_{q1}$—NR—CO)$_{24}$—, where R$_3$ and R$_4$ can be H, —COOH, or OH, q$_1$ is 1-6 and R is defined as above.
75. Insulin derivative according to any of paragraphs 48-69, wherein Y is a bond.
76. Insulin derivative according to any of paragraphs 48-75, wherein Q is —(CH$_2$)$_r$— where r is an integer from 4 to 22.
77. Insulin derivative according to paragraph 76, wherein r is an integer from 8 to 20.
78. Insulin derivative according to paragraphs 76-77, wherein r is an integer from 10 to 18.
79. Insulin derivative according to paragraphs 76-78, wherein r is 12, 13, 14, 15, 16, 17 or 18.
80. Insulin derivative according to any of paragraphs 48-75, wherein Q is a divalent chain comprising 1, 2 or 3 —CH=CH— groups and a number of —CH$_2$— groups sufficient to give a total number of carbon atoms in the chain in the range of 4 to 22.
81. Insulin derivative according to any of paragraphs 48-75, wherein Q is a divalent chain of the formula:

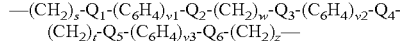

wherein Q$_1$-Q$_6$ independently of each other can be O; S or a bond; where s, w, t and z independently of each other are zero or an integer from 1 to 10 so that the sum of s, w, t and z is in the range from 4 to 22, and v$_1$, v$_2$, and v$_3$ independently of each other can be zero or 1.
82. Insulin derivative according to paragraph 81, wherein s is 1 or 2.
83. Insulin derivative according to paragraph 81, wherein s is 9, 10 or 11.
84. Insulin derivative according to any of paragraphs 81-83, wherein v$_1$ is 1 or 2.

85. Insulin derivative according paragraphs 81-84, wherein Q$_1$, Q$_2$, Q$_5$ and Q$_6$ are all a bond.
86. Insulin derivative according to any of paragraphs 81-84, wherein Q$_1$ is S or O.
87. Insulin derivative according to any of paragraphs 81-86, wherein w is 2.
88. Insulin derivative according to paragraph 87, wherein v$_2$ is 1 and t is 1.
89. Insulin derivative according to any of paragraphs 48-88, wherein Z is —COOH.
90. Insulin derivative according to any of paragraphs 48-88, wherein Z is —CO-Asp.
91. Insulin derivative according to any of paragraphs 48-88, wherein Z is —CO-Glu.
92. Insulin derivative according to any of paragraphs 48-88, wherein Z is —CO-Gly.
93. Insulin derivative according to any of paragraphs 48-88, wherein Z is —CO-Sar.
94. Insulin derivative according to any of paragraphs 48-88, wherein Z is —CH(COOH)$_2$.
95. Insulin derivative according to any of paragraphs 48-88, wherein Z is —N(CH$_2$COOH)$_2$.
96. Insulin derivative according to any of paragraphs 48-88, wherein Z is —SO$_3$H.
97. Insulin derivative according to any of paragraphs 48-88, wherein Z is —PO$_3$H$_2$.
98. Insulin derivative according to any of paragraphs 48-88, wherein Z is —O—SO$_3$H.
99. Insulin derivative according to any of paragraphs 48-88, wherein Z is —O—PO$_3$H$_2$.
100. Insulin derivative according to any of paragraphs 48-88, wherein Z is -tetrazol-5-yl.
101. Insulin derivative according to any of paragraphs 48-88, wherein Z is —O—W$_1$, where W$_1$ is arylene or heteroarylene substituted with one or two groups selected from —COOH, —SO$_3$H, and —PO$_3$H$_2$ and tetrazol-5-yl.
102. Insulin derivative according to any of the paragraphs 1-101, wherein the parent insulin is an insulin analogue, which do not have a Lys residue at position B29 of the B-chain.
103. Insulin derivative according to any of the paragraphs 1-102, wherein the parent insulin is human insulin or porcine insulin, wherein the Lys residue in position B29 is substituted and a Lys residue is inserted in a position in the A-chain or B-chain except position B29.
104. Insulin derivative according to paragraphs 1 and 102-103, wherein the amino acid residue at one of the positions A8, A9, A10, A12, A14, A15, A17, A18, A21, A22, A23 or A24 of the A-chain of the parent insulin is a Lys residue.
105. Insulin derivative according to paragraphs 1 and 102-103, wherein the amino acid residue at one of the positions position B1, B2, B3, B4, B20, B21 or B22 of the B-chain of the parent insulin is a Lys residue.
106. Insulin derivative according to paragraph 102-105, wherein the amino acid residue at position B30 of the parent insulin has been deleted.
107. Insulin derivative according to paragraph 102-106, wherein the amino acid residue at position B1 of the parent insulin has been deleted.
108. Insulin derivative according to paragraph 102-107, wherein the amino acid residue in position A21 of the parent insulin is Gly or Asn.
109. Insulin derivative according to paragraph 102-108, wherein the amino acid residue at position B3 of the parent insulin is Lys.

110. Insulin derivative according to paragraph 102-109, wherein the amino acid residue at position B28 of the parent insulin is Asp.

111. Insulin derivative according to any of paragraphs 102-110, wherein the amino acid residue at position B29 of the parent insulin is Pro or Thr.

112. A zinc complex of an insulin derivative according to any one of the preceding paragraphs wherein two zinc ions, three zinc ions four zinc ions, five zinc ions, six zinc ions, seven zinc ions, eight zinc ions, nine zinc ions, ten six zinc ions, eleven six zinc ions or twelve six zinc ions are bound per six molecules of insulin derivative.

113. A pharmaceutical composition for the treatment of diabetes in a patient in need of such treatment, comprising a therapeutically effective amount of an insulin derivative according to any of the preceding paragraphs optionally together with a pharmaceutically acceptable carrier.

114. A pharmaceutical composition for the treatment of diabetes in a patient in need of such treatment, comprising a therapeutically effective amount of an insulin derivative according to any of the preceding paragraphs in mixture with an insulin or an insulin analogue which has a rapid onset of action optionally together with a pharmaceutically acceptable carrier.

115. A method for producing a pharmaceutical composition according to paragraphs 113-114 or a zinc complex of an insulin derivative according to paragraph 112, wherein up to about 12 zinc ions per 6 molecules of insulin derivative are added to the pharmaceutical composition.

116. A method according to paragraph 115, wherein the up to about 12 zinc ions per 6 molecules of insulin derivative are added to the pharmaceutical composition after addition of a preservative.

117. A method of treating diabetes in a patient in need of such a treatment, comprising administering to the patient a therapeutically effective amount of an insulin derivative according to any of paragraphs 1-111 optionally together with a pharmaceutically acceptable carrier.

118. A method of treating diabetes in a patient in need of such a treatment, comprising administering to the patient a therapeutically effective amount of an insulin derivative according to any of paragraphs 1-111 in mixture with an insulin or an insulin analogue which has a rapid onset of action optionally together with a pharmaceutically acceptable carrier.

119. A method according to paragraphs 117-118 for pulmonary treatment of diabetes.

120. Use of an insulin derivative according to any of paragraphs 1-111 for the manufacture of a pharmaceutical composition for the use in the treatment of type 1 diabetes, type 2 diabetes and other states that cause hyperglycaemia.

121. Use of an insulin derivative according to any of paragraphs 1-111 in mixture with an insulin or an insulin analogue which has a rapid onset of action for the manufacture of a pharmaceutical composition for the use in the treatment of type 1 diabetes, type 2 diabetes and other states that cause hyperglycaemia.

122. A mixture of an insulin derivative according to any of paragraphs 1-111 and a rapid acting insulin analogue selected from the group consisting of AspB28 human insulin; LysB28ProB29 human insulin and LysB3GluB29 human insulin.

123. Insulin derivative according to paragraph 1, wherein the insulin derivative is selected from the group consisting of
$N^{\epsilon A9}$-myristyl LysA9 ArgB29 desB30 human insulin,
$N^{\epsilon B3}$-myristyl LysB3 ArgB29 desB30 human insulin,
$N^{\epsilon B22}$-myristyl LysB22 ArgB29 desB30 human insulin,
$N^{\epsilon A15}$-myristyl LysA15 ArgB29 desB30 human insulin,
$N^{\epsilon A18}$-myristyl LysA18 ArgB29 desB30 human insulin,
$N^{\epsilon A22}$-myristyl LysA22 ArgB29 desB30 human insulin,
$N^{\epsilon A9}$-ω-carboxypentadecanoyl-γ-Glu LysA9 ArgB29 desB30 human insulin,
$N^{\epsilon B3}$-ω-carboxypentadecanoyl-γ-Glu LysB3 ArgB29 desB30 human insulin,
$N^{\epsilon B22}$-ω-carboxypentadecanoyl-γ-Glu LysB22 ArgB29 desB30 human insulin,
$N^{\epsilon A15}$-ω-carboxypentadecanoyl-γ-Glu LysA15 ArgB29 desB30 human insulin,
$N^{\epsilon A18}$-ω-carboxypentadecanoyl-γ-Glu LysA18 ArgB29 desB30 human insulin,
$N^{\epsilon A22}$-ω-carboxypentadecanoyl-γ-Glu LysA22 ArgB29 desB30 human insulin.

124. Insulin derivative as described in the examples.

The invention will further be summarized in the following paragraphs:

1a. Insulin derivatives having a side chain attached either to an ε-amino group of a Lys residue present in the A-chain at position A8, A9, A10, A12, A14, A15, A17, A18, A21, A22, A23 or A24 or to an ε-amino group of a Lys residue in the B-chain at position B1, B2, B3, B4, B20, B21 or B22 of the parent insulin provided that when B3 is Lys, then B29 is not Glu 2a. An insulin derivative according to paragraph 1a, wherein the sidechain is a lipophilic group containing from 6 to 40 carbon atoms.

3a. An insulin derivative according to paragraph 2a, wherein the sidechain comprises an acyl group having from 6 to 40, carbon atoms, preferably 12 to 36, carbon atoms.

4a. An insulin derivative according to paragraph 3a, in which the acyl group is $CH_3-(CH_2)_n-CO-$, where $4 \leq n \leq 38$.

5a. An insulin derivative according to paragraph 3a, in which the acyl group is $(COOH)-(CH_2)_n-CO-$, where $4 \leq n \leq 38$.

6a. An insulin derivative according to paragraph 3a, in which the acyl group is $(NH_2-CO)-(CH_2)_n-CO-$, where $4 \leq n \leq 38$.

7a. An insulin derivative according to paragraph 3a, in which the acyl group is $HO-(CH_2)_n-CO-$, where $4 \leq n \leq 38$.

8a. An insulin derivative according to paragraph 3a, in which the acyl group is 5-α lithocholic acid or 5-β lithocholic acid.

9a. An insulin derivative according to paragraph 3a, in which the acyl group is 5-α or 5-β isomers of cholic acid, hyocholic acid, deoxycholic acid, chenodeoxycholic acid, ursodeoxycholic acid, hyodeoxycholic acid or cholanic acid.

10a. An insulin derivative according to paragraph 3a, in which the acyl group is a 5-α or 5-β isomer of dehydrolithocholic acid.

11a. An insulin derivative according to paragraph 3a, in which the acyl group is fusidic acid, a fusidic acid derivative or glycyrrhetinic acid.

12a. An insulin derivative according to paragraph 1a where the side chain is of the general formula:

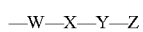

wherein W is:
an α-amino acid residue having a carboxylic acid group in the side chain which residue forms, with one of its carboxylic acid groups, an amide group with the ε-amino group of a Lys residue present in the A- or the B-chain of the parent insulin; or a chain composed of two, three or four α-amino acid residues linked together via amide bonds, which chain—via an amide bond—is linked to the ε-amino group of a Lys residue present in the A- or the B-chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or a covalent bond from X to the ε-amino group of a Lys residue present in the A- or the B-chain of the parent insulin;

X is:
—CO—;
—CH(COOH)CO—;
—N(CH$_2$COO$\overline{\text{H}}$)CH$_2$CO—;
—N(CH$_2$COOH)CH$_2$$\overline{\text{C}}$ON(CH$_2$COOH)CH$_2$$\underline{\text{CO}}$—;
—N(CH$_2$CH$_2$COOH)CH$_2$CH$_2$CO—;
—N(CH$_2$CH$_2$COOH)CH$_2$CH$_2$$\overline{\text{C}}$ON(CH$_2$CH$_2$COOH)CH$_2$CH$_2$CO—;
—NH$\overline{\text{C}}$H(COOH)(CH$_2$)$_4$NHCO—;
—N(CH$_2$CH$_2$COOH)CH$_2$C$\overline{\text{O}}$—; or
—N(CH$_2$COOH)CH$_2$CH$_2$$\overline{\text{C}}$O—.

that
a) when W is an amino acid residue or a chain of amino acid residues, via a bond from the underscored carbonyl carbon forms an amide bond with an amino group in W, or
b) when W is a covalent bond, via a bond from the underscored carbonyl carbon forms an amide bond with the ε-amino group of a Lys residue present in the A- or the B-chain of the parent insulin;

Y is:
—(CH$_2$)$_m$— where m is an integer in the range of 6 to 32;
a divalent hydrocarbon chain comprising 1, 2 or 3 —CH=CH— groups and a number of —CH$_2$— groups sufficient to give a total number of carbon atoms in the chain in the range of 10 to 32;
a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H;
and any Zn$^{2+}$ complexes thereof.

13a. An insulin derivative according to paragraphs 3a-12a, in which the acyl group is linked to the lysine residue using an amino acid as linker.

14a. An insulin derivative according to paragraph 13a, in which the amino acid link is α-glutamyl or γ-glutamyl bonded or A- or α-aspartyl bonded.

15a An insulin derivative according to paragraph 13a, in which the amino acid link is γ-aminobutanoyl bonded, β-alanyl bonded, α-amido-γ-glutamyl bonded, or α-amido-β-aspartyl bonded.

16a. Insulin derivative according to paragraph 2a, wherein the side chain comprises a fatty acid or a fatty diacid 17a. Insulin derivative according to paragraph 2a, wherein the lipophilic group can be negatively charged.

18a. Insulin derivative according to paragraph 17a, wherein the side chain comprises a lipophilic amino acid residue.

19a. Insulin derivative according to paragraph 17a, wherein the side chain comprises an amino acid residue.

20a. Insulin derivative according to any of the preceding paragraphs, wherein the parent insulin is desB30 human insulin, ArgB29 human insulin or ArgB29desB30 human insulin.

21a. Insulin derivative as described in the examples.

22a. A zinc complex of an insulin derivative according to any one of the preceding paragraphs wherein up to 12 zinc atoms are bound per 6 insulin derivatives.

23a. A pharmaceutical composition for the treatment of diabetes in a patient in need of such treatment, comprising a therapeutically effective amount of an insulin derivative according to any of the paragraphs 1a-21a or a zinc complex of the insulin derivative according to paragraph 22a together with a pharmaceutically acceptable carrier.

24a. A pharmaceutical composition for the treatment of diabetes in a patient in need of such treatment, comprising a therapeutically effective amount of an insulin derivative according to any of the paragraphs 1a-21a or a zinc complex of the insulin derivative according to paragraph 22a in mixture with an insulin or an insulin analogue which has a rapid onset of action, together with a pharmaceutically acceptable carrier.

25a. A pharmaceutical composition according to paragraph 23a or 24a intended for pulmonal administration.

26a. A pharmaceutical composition according to paragraphs 23a-25a comprising up to about 12 zinc ions per 6 molecules of insulin derivative.

27a. A method for producing a pharmaceutical composition according to paragraphs 23a-25a, wherein up to about 12 zinc ions per 6 molecules of insulin derivative are added to the pharmaceutical composition after addition of a preservative.

28a. A method of treating diabetes in a patient in need of such a treatment, comprising administering to the patient a therapeutically effective amount of an insulin derivative according to paragraphs 1a-21a or a zinc complex of the insulin derivative according to paragraph 22a together with a pharmaceutically acceptable carrier and pharmaceutical acceptable additives.

29a. A method of treating diabetes in a patient in need of such a treatment, comprising administering to the patient a therapeutically effective amount of an insulin derivative according to paragraphs 1a-21a or a zinc complex of the insulin derivative according to paragraph 22a in mixture with an insulin or an insulin analogue which has a rapid onset of action, together with a pharmaceutically acceptable carrier and pharmaceutical acceptable additives.

EXAMPLES

General Procedures

Construction of Expression Vectors Transformation of the Yeast Cells and Expression of the Insulin Precursors of the Invention All expressions plasmids are of the C—POT type, similar to those described in EP 171142, which are characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator. These sequences are similar to the corresponding sequences in plasmid pKFN1003 (described in WO 90/10075) as are all sequences except the sequence of the EcoRI-XbaI fragment encoding the fusion protein of the leader and the insulin product. In order to express different fusion proteins, the EcoRI-XbaI fragment of pKFN1003 is simply replaced by an EcoRI-XbaI fragment encoding the leader-insulin fusion of interest. Such EcoRI-XbaI fragments may be synthesized using synthetic oligonucleotides and PCR according to standard techniques.

Yeast transformants were prepared by transformation of the host strain *S. cerevisiae* strain MT663 (MATa/MATαpep-4-3 1pep-4-3 HIS4/his4 tpi::LEU2/tpi::LEU2 Cir⁺). The yeast strain MT663 was deposited in the Deutsche Sammiung von Mikroorganismen und Zelikulturen in connection with filing WO 92/11378 and was given the deposit number DSM 6278.

MT663 was grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM Na$_2$EDTA pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM Na$_2$EDTA, 0.1 M sodium citrate, pH 05.8, and 2 mg Novozym®234. The suspension was incubated at 30° C. for 30 minutes, the cells collected by centrifugation, washed in 10 ml of 1.2 M sorbitol and 10 ml of CAS (1.2 M sorbitol, 10 mM CaCl$_2$, 10 mM Tris HCl (pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM CaCl$_2$, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM CaCl$_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) Methods in Yeast Genetics, Cold Spring Harbor Laboratory) containing 1.2 M sorbitol plus 2.5% agar) at 52° C. was added and the suspension poured on top of plates containing the same agar-solidified, sorbitol containing medium. *S. cerevisiae* strain MT663 transformed with expression plasmids was grown in YPD for 72 h at 30° C.

Production, Purification and Characterization of the Insulin Derivatives of the Invention A number of insulin precursors were produced as described above and isolated from the culture medium and purified. The insulin precursors were acylated and processed as described in the below examples to produce the final insulin derivatives. These insulin derivatives were tested for biological insulin activity as measured by binding affinity to the human insulin receptor relative to that of human insulin as described below.

The following examples refer to intermediate compounds and final products identified in the specification and in the examples. The preparation of the insulin derivatives of the present invention is described in detail using the following examples, but the chemical reactions and purification schemes described are disclosed in terms of their general applicability to the preparation of the insulin derivatives of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

The insulin derivatives of the invention can be purified by employing one or more of the following procedures which are typical within the art. These procedures can—if needed—be modified with regard to gradients, pH, salts, concentrations, flow, columns and so forth. Depending on factors such as impurity profile, solubility of the insulins in question etcetera, these modifications can readily be recognised and made by a person skilled in the art.

Example 1

Synthesis of N$^{\epsilon A9}$-myristyl LysA9 ArgB29 desB30 Human Insulin

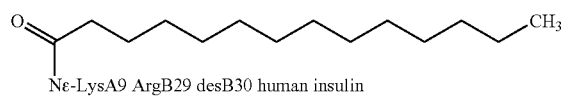

Nε-LysA9 ArgB29 desB30 human insulin

Step 1: Synthesis of Myristic Acid N-hydroxysuccinimide Ester

Synthesis of the acylation reagent myristic acid N-hydroxysuccinimide ester was performed as described in B. Faroux-Corlay et al., *J. Med. Chem.* 2001, 44, 2188-2203.

Step 2: Preparation and Purification of the Insulin Precursor LysA9 ArgB29 desB30 B'A The insulin precursor LysA9 ArgB29 desB30 B'A was purified as described in the purification steps A to C below.

Purification step A: Capture

In step A 10.75 liters of cleared culture media was diluted by addition of 4.5 liters of 99% ethanol, to give a total volume of 15.25 liters containing 30 vol % ethanol (conductivity 2.7 mS/cm, pH=3.4). A 300 ml SP Big Beads Sepharose column (100-300 μm, Amersham Biosciences) was equilibrated with 1 liter of 0.1 M citric acid pH 3.5 (flow app. 20 ml/min), before loading the 15.25 liters of prepared culture media over night (flow app. 10 ml/min). After loading the column was again washed with 1 liter of 0.1 M citric acid pH 3.5 followed by 1 liter of 40 vol % ethanol (flow app. 20 ml/min). The bound insulin precursor LysA9 ArgB29 desB30 B'A was then eluted with 1.5 liters of 0.2 M sodium acetate, 35 vol % ethanol, pH 5.75 (flow: 1.5 ml/min, volume of eluted precursor: 400 ml, amount of precursor: 220 mg).

Purification step B: Reverse-Phase HPLC

In step B the eluate was evaporated to dryness and the pellet re-dissolved in 0.25 M acetic acid. The pH was lowered further to 1.5 immediately before purification by reverse-phase HPLC on a C18 column (ODDMS C18, 20×250 mm, 200 Å, 10 μm, FeF Chemicals A/S). Before application to the column the precursor solution was sterile filtrated (22 μm, Low Protein Binding Durapore® (PVDF), Millipore). A gradient from 15% B to 50% B was run over the column, where Buffer A: 0.2 M (NH$_4$)$_2$SO$_4$, 0.04 M ortho-phosphoric acid, 10 vol % ethanol, pH 2.5 and Buffer B: 70 vol % ethanol. The gradient was run over 120 min with a flow of 5 ml/min, column temperature at 40° C. The insulin precursor LysA9 ArgB29 desB30 B'A was eluted at approximately 35% B and pooled (total volume 75 ml).

Purification step C: De-Salting by Gelfiltration

In step C the ethanol content in the eluate from reverse-phase HPLC was lowered to less than 5 vol % using a rotary evaporator (new volume: ~50 ml). A 1000 ml G25 Sephadex column (5×55 cm, Amersham Biosciences) was washed in 0.5 M acetic acid and the insulin precursor LysA9 ArgB29 desB30 B'A was then applied to the column and thereby de-salted by gelfiltration in 0.5 M acetic acid. The insulin precursor was followed by UV detection at 280 nm, while the salt was followed by conductivity measurement. Immediately after de-salting the insulin precursor was lyophilized (160 mg by weight, 5759.87 m/z).

Step 3: Synthesis of N$^{εA9}$-myristyl LysA9 ArgB29 desB30 B'A Precursor 30 mg of lyophilized insulin precursor LysA9 ArgB29 desB30 B'A was dissolved in 5 ml of 50 mM boric acid pH 2.6. The pH was then raised to 10.2 with a few drops of 1 M NaOH. 4 mg of the acylation reagent myristic acid N-hydroxysuccinimide ester was dissolved in 3.4 ml CH$_3$CN under careful heating to approximately 50° C. 3.2 ml of acylation reagent solution was then added to the insulin precursor solution while stirring (hereby the acylation reagent was 1.75 times in excess). After incubation with stirring for 60 minutes at room temperature, the reaction was stopped by addition of 2.1 ml 0.2 M ethanolamine pH 9.0. After 10 minutes incubation at room temperature the pH was adjusted to 6.4, whereby the acylated insulin precursor N$^{εA9}$-myristyl LysA9 ArgB29 desB30 B'A precipitated. The precipitate was stored at 4° C. over night (amount of precipitate: 23 mg).

Step 4: Production of N$^{εA9}$-myristyl LysA9 ArgB29 desB30 Human Insulin

The 23 mg of N$^{εA9}$-myristyl LysA9 ArgB29 desB30 B'A precipitate was dissolved in 4.2 ml 50 mM glycine, 20 vol % ethanol pH 10.0. 3.6 mg of lyophilized porcine trypsin (Novo Nordisk A/S) was also dissolved in 3.5 ml 50 mM glycine, 20 vol % ethanol pH 10.0. Of this trypsin solution 0.5 ml was then added to the insulin precursor solution (hereby the insulin precursor was in 200 times excess). The mixture was then incubated at room temperature for 15 minutes, after which the trypsin activity was stopped by lowering the pH<3 (pH=2.08 with 0.5 M acetic acid).

The acylated insulin analogue N$^{εA9}$-myristyl LysA9 ArgB29 desB30 human insulin was then purified (removing trypsin and any un-acylated, doubly-acylated etc. or un-cleaved insulin molecules) by reverse-phase HPLC. A 40% B to 100% B gradient was applied to a C4 column (Jupiter C4, 5 μm, 300 Å, 10×250 mm, Phenomenex), where Buffer A: 10 mM Tris, 15 mM (NH$_4$)HCO$_3$, 10 vol % ethanol, pH 8.5 and Buffer B: 70 vol % ethanol. The gradient was run over 120 min with a flow of 2 ml/min, column temperature at 40° C., and column size 1×25 cm. The N$^{εA9}$-myristyl LysA9 ArgB29 desB30 human insulin was eluted at 70% B (volume of eluated analogue: 15 ml). The analogue was precipitated by lowering the pH to approximately 6, re-dissolved in 2 ml of 0.5 M acetic acid and lyophilized (amount of analogue by weight: 9.3 mg by weight, LCMS: 5988.04 m/z).

Example 2

Synthesis of N$^{εA9}$-ω-carboxypentadecanoyl-γ-Glu LysA9 ArgB29 desB30 Human Insulin Step 1: Preparation of ω-carboxypentadecanoyl-L-Glu(OSu)-OH The acylating reagent ω-carboxypentadecanoyl-L-Glu (OSu)-OH was prepared essentially as described for octadecandioyl-L-Glu(OSu)-OH (ω-carboxyheptadecanoyl-L-Glu (OSu)-OH) in WO-2005012347-A2, starting from hexadecanedioic acid instead of octadecanedioic acid.

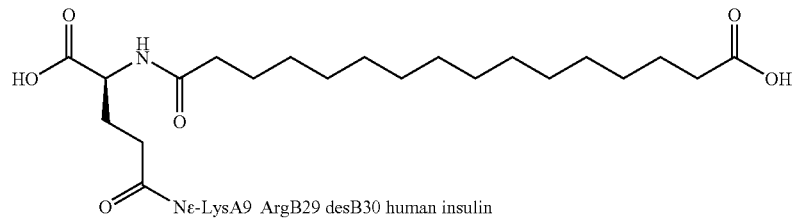

Step 2: Preparation and Purification of the Insulin Precursor LysA9 ArgB29 desB30 B'A The insulin precursor was purified as described under step 2 in example 1.

Step 3: Synthesis of N$^{εA9}$-ω-carboxypentadecanoyl-γ-Glu LysA9 ArgB29 desB30 B'A Precursor 40 mg of lyophilized insulin precursor LysA9 ArgB29 desB30 B'A was dissolved in 2 ml of 100 mM Na$_2$CO$_3$ pH 10.8. 13 mg of the acylation reagent co-carboxypentadecanoyl-L-Glu(OSu)-OH was suspended in 500 μl CH$_3$CN. The acylation reagent was then dissolved by addition of 70 μl NMP. The 570 μl of acylation reagent solution was then added slowly to the insulin precursor solution while stirring (hereby the acylation reagent was 2.5 times in excess). After incubation with stirring for 60 minutes at room temperature, the reaction was stopped by adjusting pH to approximately 5, whereby the acylated insulin precursor N$^{εA9}$-ω-carboxypentadecanoyl-γ-Glu LysA9 ArgB29 desB30 B'A precipitated. The precipitate was stored at 4° C. over night (LC-MS: 6154.93 m/z).

Step 4: Production of N$^{εA9}$-ω-carboxypentadecanoyl-γ-Glu LysA9 ArgB29 desB30 Human Insulin The N$^{εA9}$-ω-carboxypentadecanoyl-γ-Glu LysA9 ArgB29 desB30 B'A precipitate was dissolved in 3 ml 50 mM glycine, 20 vol % ethanol pH 10.0.1 mg of lyophilized porcine trypsin (Novo Nordisk A/S) was also dissolved in 1.5 ml 50 mM glycine, 20 vol % ethanol pH 10.0, and was then added to the insulin precursor solution (hereby the insulin precursor was 300 times in excess). The reaction was then incubated at room temperature for 15 minutes, after which the trypsin activity was stopped by lowering the pH<3.

The acylated insulin analogue $N^{\epsilon A9}$-ω-carboxypentadecanoyl-γ-Glu LysA9 ArgB29 desB30 human insulin was then purified (removing trypsin and any un-acylated, doubly-acylated etc. or un-cleaved insulin molecules) by reverse-phase HPLC. A 25% B to 55% B gradient was applied to a Fuji C4 column (15 μm, 200 Å, 10×250 mm, FeF Chemicals A/S), where Buffer A: 10 mM Tris, 15 mM $(NH_4)HCO_3$, 10 vol % ethanol, pH 8.5 and Buffer B: 70 vol % ethanol. The gradient was run over 100 min with a flow of 3 ml/min at room temperature. The $N^{\epsilon A9}$-ω-carboxypentadecanoyl-γ-Glu LysA9 ArgB29 desB30 human insulin was eluted at approximately 48% B (17 mg of derivative). The analogue was precipitated by lowering the pH below 5, re-dissolved in 2 ml of 0.5 M acetic acid and lyophilized (LC-MS: 6173

Example 3

Synthesis of $N^{\epsilon B3}$-ω-carboxypentadecanoyl-γ-Glu LysB3 ArgB29 desB30 Human Insulin

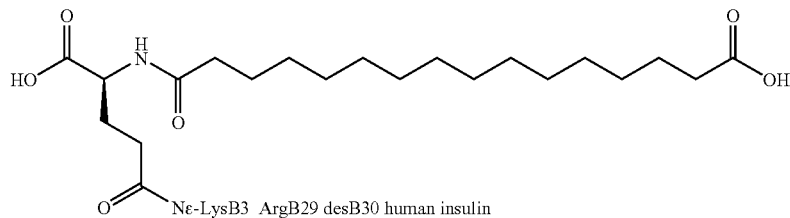

Step 1: Preparation of ω-carboxypentadecanoyl-L-Glu(OSu)-OH

Preparation of the acylation reagent ω-carboxypentadecanoyl-L-Glu(Osu)-OH was performed as described under example 2.

tep 2: Preparation and Purification of the Insulin Precursor LysB3 ArgB29 desB30 B'A The insulin precursor was purified essentially as described in under step 2 in example 1, i.e. with a capture step, followed by reverse-phase HPLC, and a final desalting. Immediately after de-salting the insulin precursor was lyophilized (LC-MS: 5731.34 m/z).

Step 3: Synthesis of $N^{\epsilon B3}$-ω-carboxypentadecanoyl-γ-Glu LysB3 ArgB29 desB30 B'A Precursor The synthesis of the insulin precursor $N^{\epsilon B3}$-ω-carboxypentadecanoyl-γ-Glu LysB3 ArgB29 desB30 B'A was performed essentially as described in step 3 of example 2 (LC-MS: 6128.2 m/z).

Step 4: Production of $N^{\epsilon B3}$-ω-carboxypentadecanoyl-γ-Glu LysB3 ArgB29 desB30 Human Insulin The $N^{\epsilon B3}$-ω-carboxypentadecanoyl-γ-Glu LysB3 ArgB29 desB30 B'A was cleaved by trypsin essentially as described for $N^{\epsilon A9}$-ω-carboxypentadecanoyl-γ-Glu LysA9 ArgB29 desB30 B'A, step 4 in example 2.

The acylated insulin analogue $N^{\epsilon B3}$-ω-carboxypentadecanoyl-γ-Glu LysB3 ArgB29 desB30 human insulin was then purified by reverse-phase HPLC. First the reaction mixture from the trypsin cleavage was diluted by adding water to 10% ethanol (4.5 ml) and 175 μl PMSF (1 mg/ml) was added to inhibit trypsin. The pH was adjusted to 8 to dissolve the $N^{\epsilon B3}$-ω-carboxypentadecanoyl-γ-Glu LysB3 ArgB29 desB30 human insulin. A 20% B to 50% B gradient was applied to a Fuji C4 column (15 μm, 200 Å, 10×250 mm, FeF Chemicals A/S), where Buffer A: 10 mM Tris, 15 mM $(NH_4)HCO_3$, 10 vol % ethanol, pH 8.5 and Buffer B: 70 vol % ethanol. The gradient was run over 160 min with a flow of 3 ml/min at room temperature. The $N^{\epsilon B3}$-ω-carboxypentadecanoyl-γ-Glu LysB3 ArgB29 desB30 human insulin was eluted at app. 30% B.

The derivative was further purified by reverse-phase HPLC using an analytical Jupiter C4 column (5 μm, 300 Å, 4.6×150 mm, Phenomenex). A 20% B to 50% B gradient was applied to the column, where Buffer A: 12.5 mM Tris, 20 mM $(NH_4)SO_4$, 20 vol % $CH_3CN$, pH 7 and Buffer B: 80 vol % $CH_3CN$. The sample from the above preparative HPLC was divided into approximately 10 subsamples, and each subsample was purified on the analytical HPLC scale. Total volume after purification: 20 ml, 91% purity.

The analogue was precipitated by lowering the pH to 5.12, and the pellet was lyophilized (1 mg, LC-MS: 6148.4 m/z).

Example 4

Synthesis of $N^{\epsilon B3}$-myristyl LysB3 ArgB29 desB30 Human Insulin

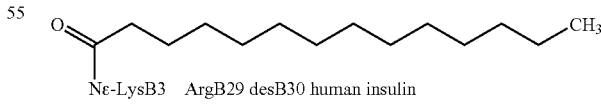

Preparation and purification of the LysB3 ArgB29 desB30 B'A precursor is described in example 3. Synthesis of the $N^{\epsilon B3}$-myristyl LysB3 ArgB29 desB30 B'A precursor and the following cleavage by trypsin to produce the final product, $N^{\epsilon B3}$-myristyl LysB3 ArgB29 desB30 human insulin, was performed essentially as described in example 1. LC-MS: Intact derivative: 5959.0 m/z, B-chain of reduced derivative: 3581.3 m/z.

Example 5

Synthesis of $N^{\epsilon B22}$-myristyl LysB22 ArgB29 desB30 Human Insulin

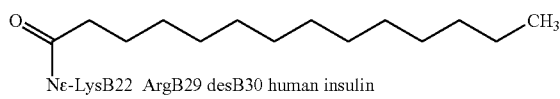

Preparation and purification of the LysB22 ArgB29 desB30 B'A precursor was done essentially as described in example 1 and 3. Synthesis of the $N^{\epsilon B22}$-myristyl LysB22 ArgB29 desB30 B'A precursor and the following cleavage by trypsin to produce the final product, $N^{\epsilon B22}$-myristyl LysB22 ArgB29 desB30 human insulin, was performed essentially as described in example 1. LC-MS: Intact derivative: 5917.2 m/z, reduced derivative: 2382.60 m/z (A-chain), 3537.70 m/z (B-chain).

Example 6

Synthesis of $N^{\epsilon B22}$-ω-carboxypentadecanoyl-γ-Glu LysB22 ArgB29 desB30 Human Insulin

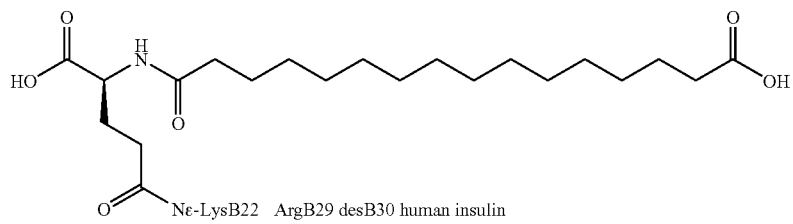

Preparation and purification of the LysB22 ArgB29 desB30 B'A precursor was done essentially as described in example 1 and 3. Synthesis of the $N^{\epsilon B22}$-ω-carboxypentadecanoyl-γ-Glu LysB22 ArgB29 desB30 B'A precursor and the following cleavage by trypsin to produce the final product, $N^{\epsilon B22}$-ω-carboxypentadecanoyl-γ-Glu LysB22 ArgB29 desB30 human insulin, was performed essentially as described in example 2 and 3. MS calculated: 6104.06 m/z.

Example 7

Synthesis of $N^{\epsilon A15}$-myristyl LysA15 ArgB29 desB30 Human Insulin

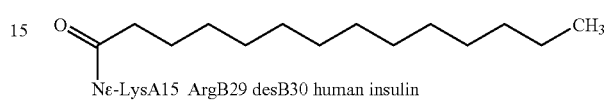

Preparation and purification of the LysA15 ArgB29 desB30 B'A precursor was done essentially as described in example 1 and 3. Synthesis of the $N^{\epsilon A15}$-myristyl LysA15 ArgB29 desB30 B'A precursor and the following cleavage by trypsin to produce the final product, $N^{\epsilon A15}$-myristyl LysA15 ArgB29 desB30 human insulin, was performed essentially as described in example 1. MALDI-MS: Intact derivative: 5946.14 m/z, B-chain of reduced derivative: 3356.23 m/z.

Example 8

Synthesis of $N^{\epsilon A15}$-ω-carboxypentadecanoyl-γ-Glu LysA15 ArgB29 desB30 Human Insulin

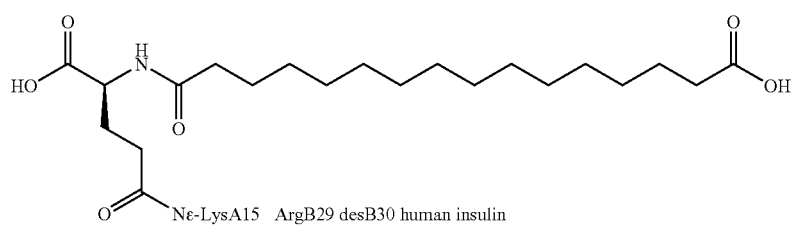

Preparation and purification of the LysA15 ArgB29 desB30 B'A precursor was done essentially as described in example 1 and 3. Synthesis of the $N^{\epsilon A15}$-ω-carboxypentadecanoyl-γ-Glu LysA15 ArgB29 desB30 B'A precursor and the following cleavage by trypsin to produce the final product, $N^{\epsilon A15}$-ω-carboxypentadecanoyl-γ-Glu LysA15 ArgB29 desB30 human insulin, was performed essentially as described in example 2 and 3. MS calculated: 6132.12 m/z.

Example 9

Synthesis of $N^{\epsilon A18}$-myristyl LysA18 ArgB29 desB30 Human Insulin

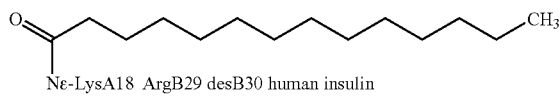
Nε-LysA18 ArgB29 desB30 human insulin

Preparation and purification of the LysA18 ArgB29 desB30 B'A precursor was done essentially as described in example 1 and 3. Synthesis of the $N^{\epsilon A18}$-myristyl LysA18 ArgB29 desB30 B'A precursor and the following cleavage by trypsin to produce the final product, $N^{\epsilon A18}$-myristyl LysA18 ArgB29 desB30 human insulin, was performed essentially as described in example 1. LC-MS: Intact derivative: 5959.5 m/z, B-chain of reduced derivative: 3355.50 m/z.

Example 10

Synthesis of $N^{\epsilon A18}$-ω-carboxypentadecanoyl-γ-Glu LysA18 ArgB29 desB30 Human Insulin

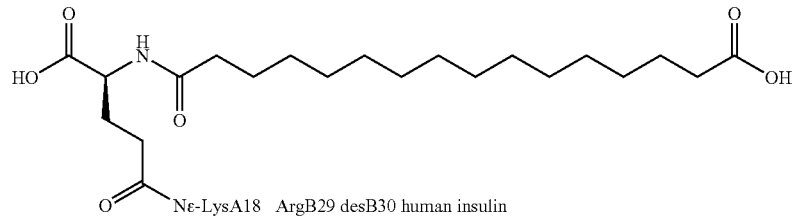
Nε-LysA18 ArgB29 desB30 human insulin

Preparation and purification of the LysA18 ArgB29 desB30 B'A precursor was done essentially as described in example 1 and 3. Synthesis of the $N^{\epsilon A18}$-ω-carboxypentadecanoyl-γ-Glu LysA18 ArgB29 desB30 B'A precursor and the following cleavage by trypsin to produce the final product, $N^{\epsilon A18}$-ω-carboxypentadecanoyl-γ-Glu LysA18 ArgB29 desB30 human insulin, was performed essentially as described in example 2 and 3. MALDI-MS: 6146.96 m/z.

Example 11

Synthesis of $N^{\epsilon A22}$-myristyl LysA22 ArgB29 desB30 Human Insulin

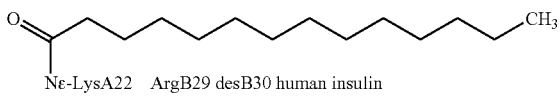
Nε-LysA22 ArgB29 desB30 human insulin

Preparation and purification of the LysA22 ArgB29 desB30 B'A precursor was done essentially as described in example 1 and 3. Synthesis of the $N^{\epsilon A22}$-myristyl LysA22 ArgB29 desB30 B'A precursor and the following cleavage by trypsin to produce the final product, $N^{\epsilon A22}$-myristyl LysA22 ArgB29 desB30 human insulin, was performed essentially as described in example 1. LC-MS: 6072.3 m/z.

Example 12

Synthesis of $N^{\epsilon A18}$-ω-carboxypentadecanoyl-γ-Glu LysA22 ArgB29 desB30 Human Insulin

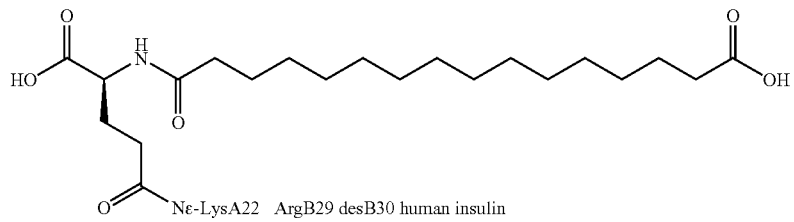

Preparation and purification of the LysA22 ArgB29 desB30 B'A precursor was done essentially as described in example 1 and 3. Synthesis of the $N^{\epsilon A18}$-ω-carboxypentadecanoyl-γ-Glu LysA22 ArgB29 desB30 B'A precursor and the following cleavage by trypsin to produce the final product, $N^{\epsilon A18}$-ω-carboxypentadecanoyl-γ-Glu LysA22 ArgB29 desB30 human insulin, was performed essentially as described in example 2 and 3. LC-MS: 6260.2 m/z.

Example 13

Synthesis of $N^{\epsilon A18}$-ω-carboxy-5-hexadecandioylaminobenzoyl LysA22 ArgB29 desB30 Human Insulin

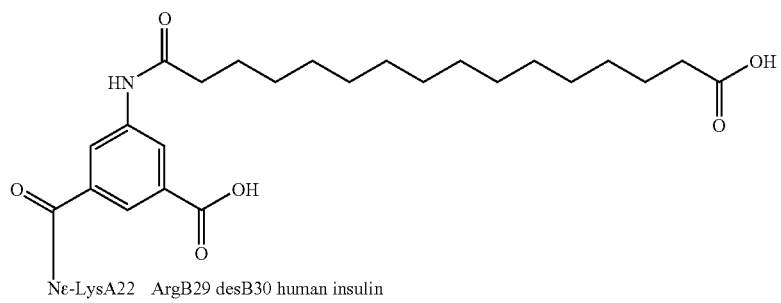

To LysA22 ArgB29 desB30 human insulin (100 mg) dissolved in 0.1 M $Na_2CO_3$ (2.25 ml) is added 1.2 equivalents 5-(15-tert-butoxycarbonylpentadecanoylamino)isophthalic acid 3-tert-butyl ester 1-(2,5-dioxopyrrolidin-1-yl) ester (prepared as described in WO 2006082204) dissolved in acetonitrile (1.13 ml). The insulin derivative is isolated by isoelectric precipitation. The dried product is treated with TFA for 30 min. The TFA is removed by evaporation. The title compound is isolated after purification by RP-HPLC, which can be performed on a Gilson 215 system using a SP 250/21 Nucleosil 300-7 C4 column and a water/acetonitril 10-80% gradient containing 0.1% TFA.

Example 14

Synthesis of $N^{\epsilon A22}$-3-carboxy-5-octadecandioylaminobenzoyl LysA22 ArgB29 desB30 Human Insulin

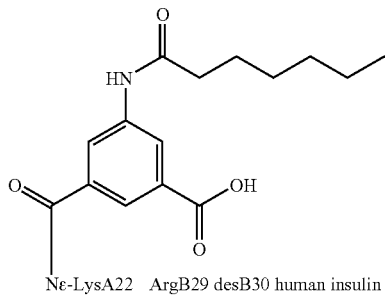

4-(17-tert-Butoxycarbonyl-heptadecanoylamino)isophthalic acid 3-tert-butyl ester 1-(2,5-dioxo-pyrrolidin-1-yl) ester is reacted with LysA22 ArgB29 desB30 human insulin followed by TFA treatment and purification similarly as described above.

Example 15

Synthesis of $N^{\epsilon A22}$-10-(3,5-Dicarboxyphenoxy)decanoyl-γ-Glu LysA22 ArgB29 desB30 Human Insulin

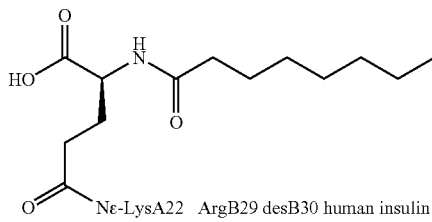

5-{9-[(S)-1-tert-Butoxycarbonyl-3-(2,5-dioxo-pyrrolidin-1-yloxycarbonyl)propylcarbamoyl]nonyloxy}isophthalic acid di-tert-butyl ester (prepared as described below) is reacted with LysA22 ArgB29 desB30 human insulin followed by TFA treatment and purification similarly as described above.

Example 16

Synthesis of $N^{\epsilon A22}$-4-[10-(3,5-Dicarboxyphenoxy)decanoylamino]-butyryl LysA22 ArgB29 desB30 Human Insulin

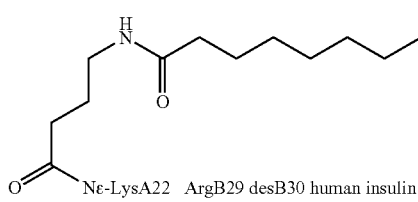

5-{9-[3-(2,5-Dioxo-pyrrolidin-1-yloxycarbonyl)-propylcarbamoyl]-nonyloxy}-isophthalic acid di-tert-butyl ester (prepared as described below) is reacted with LysA22 ArgB29 desB30 human insulin followed by TFA treatment and purification similarly as described above.

Synthesis of 5-{9-[(S)-1-tert-Butoxycarbonyl-3-(2,5-dioxo-pyrrolidin-1-yloxycarbonyl)-propylcarbamoyl]-nonyloxy}-isophthalic Acid Di-tert-butyl Ester Step 1: 3-Hydroxy-isophthalic Acid Di-tert-butyl Ester To a suspension of 5-hydroxy-isophthalic acid (1.06 g, 5.8 mmol) in dry toluene (20 ml) at 60° C. was added N,N-dimethylformamid di-tert-butyl acetal (7.0 mL, 29.2 mmol) and the temperature was raised to 100° C. Dry DMF (5 ml) was added. The mixture was stirred under nitrogen. After 2 h more N,N-dimethylformamid di-tert-butyl acetal (7.0 mL, 29.2 mmol) was added. After 3 h the reaction mixture was cooled to room temperature and filtered. The solid was purified by flash chromatography using heptane/EtOAc/acetic acid 40:20:3. The title compound was isolated, contaminated by the tri-tert-butyl ester.

LC-MS: 239, 13 (M–tBu)

Step 2: 5-(9-Methoxycarbonyl-nonyloxy)-isophthalic Acid Di-tert-butyl Ester

3-Hydroxy-isophthalic acid di-tert-butyl ester (90 mg, 0.3 mmol) was dissolved in dry acetone (5 ml), $K_2CO_3$ (90 mg, mmol) was added. The mixture was heated to reflux. The heating caused dissolution of the $K_2CO_3$. After a while, a precipitate was formed. Reflux (50° C.) was continued over night. More $K_2CO_3$ (30 mg, 0.2 mmol) and methyl 10-bromodecanoate (0.025 ml, 0.1 mmol) was added. The mixture was refluxed at 50° C. over night. To the dry reaction mixture EtOAc and water was added. After extraction, the organic layer was washed with water and brine, dried ($Na_2SO_4$) and concentrated to give the crude title compound as a clear oil.
LC-MS: m/z: 423.34 (M–tBu).

Step 3: 5-(9-Carboxy-nonyloxy)-isophthalic Acid Di-tert-butyl Ester

To a solution of 5-(9-methoxycarbonyl-nonyloxy)-isophthalic acid di-tert-butyl ester (162 mg, 0.34 mmol) in THF (2 ml) was added 1 N NaOH (0.35 ml). The mixture was refluxed for 7 h. The mixture was left at room temperature over night before concentration. To the residue EtOAc and 0.1N HCl was added. The aqueous layer was extracted twice with EtOAc. The combined organic layers were washed with brine, dried ($Na_2SO_4$) and concentrated to give a clear syrup.
LC-MS: m/z: 465.3 (M+1).

Step 4: 5-[9-(2,5-Dioxo-pyrrolidin-1-yloxycarbonyl)-nonyloxy]-isophthalic Acid Di-tert-butyl Ester To a solution of 5-(9-Carboxy-nonyloxy)-isophthalic acid di-tert-butyl ester (156 mg, 0.34 mmol) in dry THF (2 ml) was added TSTU (125 mg) and DIPEA (0.08 ml). The mixture was stirred under nitrogen over night. The mixture was concentrated. The residue was redissolved in EtOAc and filtered. The filtrate was washed with 0.1N HCl (2×), and brine (1×), dried ($Na_2SO_4$) and concentrated to give a clear syrup.
LC-MS: m/z: 562.3 (M+1).

Step 5: 5-[9-((S)-1-tert-Butoxycarbonyl-3-carboxy-propylcarbamoyl)-nonyloxy]-isophthalic Acid Di-tert-butyl Ester To a solution of 5-[9-(2,5-Dioxo-pyrrolidin-1-yloxycarbonyl)-nonyloxy]-isophthalic acid di-tert-butyl ester (62 mg, 0.11 mmol) in dry DMF (1 ml), H-Glu-OtBu (0.027 g, 0.13 mmol) and DIPEA (0.05 ml) was added. The mixture was stirred over night under nitrogen for 4 h. The mixture was concentrated. The residue was redissolved in EtOAc and washed with 0.1 N HCl (2×), brine (1×), dried ($Na_2SO_4$) and concentrated to give a syrup.
LC-MS: m/z: 650.44 (M+1).

Step 6: 5-{9-[(S)-1-tert-Butoxycarbonyl-3-(2,5-dioxo-pyrrolidin-1-yloxycarbonyl)-propylcarbamoyl]-nonyloxy}-isophthalic Acid Di-tert-butyl Ester 5-[9-((S)-1-tert-Butoxycarbonyl-3-carboxy-propylcarbamoyl)-nonyloxy]-isophthalic acid di-tert-butyl ester (70 mg, 0.11 mmol) was dissolved in dry THF (1 ml). TSTU (40 mg, 0.13 mmol) and DIPEA (0.05 ml) was added. The mixture was stirred at room temperature under nitrogen over the weekend. The mixture was concentrated. The residue was redissolved in EtOAc and filtered. The filtrate was washed with 0.1N HCl (2×), washed with brine (1×), dried ($Na_2SO_4$) and concentrated to give a clear syrup. There was still starting material present and the TSTU-treatment was repeated followed by work up to give the title compound as a clear syrup.
LC-MS: m/z: 747 (M+1).

Synthesis of 5-[9-[3-(2,5-Dioxo-pyrrolidin-1-yloxycarbonyl)-propylcarbamoyl]-nonyloxy]-isophthalic Acid Di-tert-butyl Ester

Step 1: 5-[9-(3-Carboxy-propylcarbamoyl)-nonyloxy]-isophthalic Acid Di-tert-butyl Ester 5-[9-(2,5-Dioxo-pyrrolidin-1-yloxycarbonyl)-nonyloxy]-isophthalic acid di-tert-butyl ester (100 mg, 0.18 mmol) was dissolved in dry DMF (2 ml). 4-Aminobutyric acid (GABA, 23 mg, 0.2 mmol) and DIPEA (0.05 ml) was added. The mixture was stirred under nitrogen for 2 days. The mixture was concentrated. The residue was dissolved in EtOAc and washed with 0.1 N HCl (2×) and brine (1×), dried ($Na_2SO_4$) and concentrated to give a clear syrup.
LC-MS: m/z: 550.33 (M+1).

Step 2: 5-{9-[3-(2,5-Dioxo-pyrrolidin-1-yloxycarbonyl)-propylcarbamoyl]-nonyloxy}-isophthalic Acid Di-tert-butyl Ester To a solution of 5-[9-(3-Carboxy-propylcarbamoyl)-nonyloxy]-isophthalic acid di-tert-butyl ester (62 mg, 0.11 mmol) in dry THF (2 ml) was added DIPEA (0.05 ml) and TSTU (41 mg, 0.14 mmol). The mixture was stirred at room temperature under nitrogen over night. The mixture was concentrated and EtOAc was added to the residue. The precipitate was removed by filtration. The filtrate was washed with 0.1 N HCl (2×) and brine (1×), dried ($Na_2SO_4$) and concentrated to give a clear syrup.
LC-MS: m/z: 647.29.

Example 17

Hydrophobicity of the Insulin Derivatives of the Invention

The hydrophobicity of an insulin derivative is found by reverse phase HPLC run under isocratic conditions. The elution time of the insulin derivative is compared to that of HI or another derivative with a known hydrophobicity under the same conditions. The hydrophobicity, k'rel, is calculated as: $k'rel_{deriv}=((t_{deriv}-t_0)/(t_{ref}-t_0))*k'rel_{ref}$. Using HI as reference: $k'rel_{ref}=k'rel_{HI}=1$. The void time of the HPLC system, $t_0$, is determined by injecting 5 µl of 0.1 mM $NaNO_3$. Running conditions:

| | |
|---|---|
| Column: | Lichrosorb RP-C18, 5 µm, 4 × 250 mm |
| Buffer A: | 0.1 M natrium phosphate pH 7.3, 10 vol % $CH_3CN$ |
| Buffer B: | 50 vol % $CH_3CN$ |
| Injection volume: | 5 µl |
| Run time: | max 60 minutes |

After running an initial gradient, the isocratic level for running the derivative and reference (for example HI) is chosen, and the elution times of the derivative and reference under isocratic conditions are used in the above equation to calculate $k'rel_{deriv}$.

Example 18

Insulin Receptor Binding of the Insulin Derivatives of the Invention

The affinity of the insulin derivatives of the invention for the human insulin receptor is determined by a SPA assay (Scintillation Proximity Assay) microtiterplate antibody capture assay. SPA-PVT antibody-binding beads, anti-mouse reagent (Amersham Biosciences, Cat No. PRNQ0017) are mixed with 25 ml of binding buffer (100 mM HEPES pH 7.8; 100 mM sodium chloride, 10 mM $MgSO_4$, 0.025% Tween-20). Reagent mix for a single Packard Optiplate (Packard No. 6005190) is composed of 2.4 µl of a 1:5000 diluted purified recombinant human insulin receptor (either with or without exon 11), an amount of a stock solution of A14Tyr[$^{125}$I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl reagent mix is then added to each well in the Packard Optiplate and a dilution series of the insulin derivative is made in the Optiplate from appropriate samples. The samples are then incubated for 16 hours while gently shaken. The phases are the then separated by centrifugation for 1 min and the plates counted in a Topcounter. The binding data were fitted using the nonlinear regression algorithm in the Graph-Pad Prism 2.01 (GraphPad Software, San Diego, Calif.).

Example 19

Human Serum Albumin Affinity Assay of the Insulin Derivatives of the Invention The affinity for human serum albumin of the insulin derivatives of the invention are given as the relative binding constant of the A14Tyr[$^{125}$I]-derivative to human serum albumin (HSA) immobilised on Minileak particles and measured at 23° C. as compared to insulin Detemir (equal to 1 in saline buffer): $HSA_{aff}=K_d(Detemir)/K_d(derivative)$. HSA is immobilised in the Minileak material (KemEnTec 1011F) by over night incubation at room temperature with HSA (Sigma A-1887) and PEG (Fluka 95172) in 0.3 M $NaHCO_3$ pH 8.8. After incubation the reaction is stopped by addition of 1 M ethanolamine pH 9.0, and the material is washed several times with 0.1 M Tris(HCl) pH 7.4, with 0.1 M $NaHCO_3$ pH 9.0, and with 0.1 M phosphate pH 3.0. The HSA-Minileak material is stored in 0.1 M Tris(HCl) pH 7.4, 0.02% azide. The amount of HSA immobilised on the material is assessed by incubating HSA-Minileak with $^3$H-myristic acid (PerkinElmer NET-830) and various amounts of free HSA in 0.1 M Tris(HCl) pH 7.4, 0.025% Triton-X-100 for two hours at room temperature. After centrifugation of the samples the supernatant is analysed in a scintillation-counter, and the amount of immobilised HSA is calculated.

When determining the affinity of the insulin derivatives for HSA, various amounts of HSA-Minileak is incubated with the A14Tyr[$^{125}$I]-derivative for two hours at room temperature in 0.1 M Tris(HCl) pH 7.4, 0.025% Triton-X-100. After incubation the samples are centrifuged and half the supernatant is removed to new tubes. Both half the supernatant (½S) and the remaining supernatant plus pellet (½S+P) is analysed is a gamma-counter, and these data are used for the calculation of $K_d$ for the A14Tyr[$^{125}$I]-derivative.

Example 20

Analysis of Self-Associating Properties of the Insulin Derivatives of the Invention The ability of the insulin derivatives of the invention to self-associate into large, but soluble complexes is analysed using SEC (size exclusion chromatography):

| | |
|---|---|
| Column: | Superose ™ 6 PC 3.2/30, CV = 2.4 ml (Amerham Biosciences) |
| Temperature: | 37° C. |
| SEC buffer: | 140 mM NaCl, 10 mM TrisHCl, 0.01% $NaN_3$, pH 7.5 |
| Injection volume: | 20 µl |
| Flow: | 0.04 ml/min |
| Runtime: | 80 min |

For this analysis the insulin derivatives of the invention are in a solution consisting of 0.6 mM derivative, 2.1 $Zn^{2+}$/hexamer, 16 mM phenol, 7 mM phosphate pH 7.8. The retention time of the derivative is then compared to the retention times of the following standard molecules:

| | | |
|---|---|---|
| Standard I: | HSA + HSA dimer | (66.4 kDa + 133 kDa) |
| | Co(III)hexamer | (35.0 kDa) |
| | X2 monomer | (5.9 kDa) |
| Standard II: | Blue dextran | (1.5 MDa) |
| | Thyroglobulin | (669 kDa) |
| | Ferritin | (440 kDa) |
| | Aldolase | (158 kDa) |
| | Ovalbumin | (44.5 kDa) |
| | Ribonuclease | (13.7 kDa) |

The following equation is used to determine the $K_{av}$ for the derivative:

$$K_{av}=(t-t_0)/(V_t/(f+t_d-t_0))$$

Where t is the retention time for a given peak, $t_0$ is the retention time for Blue dextran, $V_t$ is the total column volume (here 2.4 ml), f is the flow (here 0.04 ml/min), and $t_d$ is the retention time for Blue dextran without the column in the system.

The $K_{av}$ value indicates the degree of self-association of a derivative, i.e. a large $K_{av}$ similar to the $K_{av}$ for the Co(III) hexamer and X2 monomer shows low or no propensity of the derivative to form large, self-associated complexes, while very small $K_{av}$ close to zero or even negative shows great propensity of the derivative for self-association into large, soluble complexes.

| Compound | Hydrophobicity relative to human insulin | Insulin receptor affinity relative to human insulin | Self-association: $K_{av}$ (% area of peak) |
|---|---|---|---|
| Example 1 | + | ++ | Peak 1 (37%): ++ |
| | | | Peak 2 (63%): ++ |
| Example 2 | ++ | ++ | Peak 1 (64%): ++ |
| | | | Peak 2 (36%): + |
| Example 3 | ++ | +++ | — |
| Example 4 | + | +++ | ++ (100%) |
| Example 5 | + | ++ | + (100%) |
| Example 7 | + | ++ | — |
| Example 9 | + | +++ | Peak 1 (95%): ++ |
| | | | Peak 2 (5%): + |

-continued

| Compound | Hydrophobicity relative to human insulin | Insulin receptor affinity relative to human insulin | Self-association: $K_{av}$ (% area of peak) |
|---|---|---|---|
| Example 10 | +++ | | Peak 1 (65%): +<br>Peak 2 (35%): + |

Note:
Hydrophobicity relative to human insulin: k'rel < 1: +++, 1-10: ++, >10: + (HI = 1)
Insulin receptor affinity relative to human insulin: <5%: +, 5-50%: ++, >50%: +++
Self-association: $K_{av} < 0.55$: + and $K_{av} \geq 0.55$: +
($K_{av} = 0.55$ for human serum albumin (HSA), $K_{av} = 0.63$ for human insulin Co(III)hexamer, and $K_{av} = 0.72$ for the monomeric insulin analogue X2.)

Example 21

Blood Glucose Lowering Effect after I.V. Bolus Injection in Rat of the Insulin Derivatives of the Invention Male Wistar rats, 200-300 g, fasted for 18 h, was anesthetized using either Hypnorm-Dormicum s.c. (1.25 mg/ml Dormicum, 2.5 mg/ml fluanisone, 0.079 mg/ml fentanyl citrate) 2 ml/kg as a priming dose (to timepoint −30 min prior to test substance dosing) and additional 1 ml/kg every 20 minutes.

The animals are dosed with an intravenous injection (tail vein), 1 ml/kg, of control and test compounds (usual dose range 0.125-20 nmol/kg). Blood samples for the determination of whole blood glucose concentration were collected in heparinized 10 μl glass tubes by puncture of the capillary vessels in the tail tip to time −20 min and 0 min (before dosing), and to time 10, 20, 30, 40, 60, 80, 120, and 180 min after dosing. Blood glucose concentrations were measured after dilution in analysis buffer by the immobilized glucose oxidase method using an EBIO Plus autoanalyzer (Eppendorf, Germany). Mean plasma glucose concentrations courses (mean±SEM) are made for each dose and each compound.

Example 22

Determination in Pigs of $T_{50\%}$ of the Insulin Analogues of the Invention $T_{50\%}$ is the time when 50% of an injected amount of the A14 Tyr[$^{125}$I] labelled derivative of an insulin to be tested has disappeared from the injection site as measured with an external γ-counter.

The principles of laboratory animal care were followed. Specific pathogen-free LYYD, non-diabetic female pigs, cross-breed of Danish Landrace, Yorkshire and Duroc, were used (Holmeniund, Haarloev, Denmark) for pharmacokinetic and pharmacodynamic studies. The pigs were conscious, 4-5 months of age and weighing 70-95 kg. The animals were fasted overnight for 8 h before the experiment.

Formulated preparations of insulin derivatives labelled in Tyr$^{414}$ with $^{125}$I were injected sc. in pigs as previously described (Ribel, U., Jørgensen, K, Brange, J. and Henriksen, U. The pig as a model for subcutaneous insulin absorption in man. Serrano-Rios, M and Le-fèbvre, P. J. 891-896. 1985. Amsterdam; New York; Oxford, Elsevier Science Publishers. 1985 (Conference Proceeding)).

At the beginning of the experiments a dose of 60 nmol of the insulin derivative according to the invention (test compound) and a dose of 60 nmol of insulin detemir (both $^{125}$I labelled in Tyr A14) were injected at two separate sites in the neck of each pig.

The disappearance of the radioactive label from the site of sc. injection was monitored using a modification of the traditional external gamma-counting method (Ribel, U. Subcutaneous absorption of insulin analogues. Berger, M. and Gries, F. A. 70-77 (1993). Stuttgart; New York, Georg Thime Verlag (Conference Proceeding)). With this modified method it was possible to measure continuously the disappearance of radioactivity from a subcutaneous depot for several days using cordless portable device (Scancys Laboratorieteknik, Værløse, DK-3500, Denmark). The measurements were performed at 1-min intervals, and the counted values were corrected for background activity.

Example 23

Potency of the Insulin Derivatives of the Invention Relative to Human Insulin

Sprague Dawley male rats weighing 238-383 g on the experimental day were used for the clamp experiment. The rats had free access to feed under controlled ambient conditions and were fasted overnight (from 3 μm) prior to the clamp experiment.

Experimental Protocol:

The rats were acclimatized in the animal facilities for at least 1 week prior to the surgical procedure. Approximately 1 week prior to the clamp experiment Tygon catheters were inserted under halothane anaesthesia into the jugular vein (for infusion) and the carotid artery (for blood sampling) and exteriorised and fixed on the back of the neck. The rats were given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) was administered during anaesthesia and Rimadyl (1.5 mg/kg, s.c.) was administered after full recovery from the anaesthesia (2-3 h) and again once daily for 2 days.

The clamp technique employed was adapted from (1). At 7 am on the experimental day overnight fasted (from 3 μm the previous day) rats were weighed and connected to the sampling syringes and infusion system (Harvard 22 Basic pumps, Harvard, and Perfectum Hypodermic glass syringe, Aldrich) and then placed into individual clamp cages where they rested for ca. 45 min before start of experiment. The rats were able to move freely on their usual bedding during the entire experiment and had free access to drinking water. After a 30 min basal period during which plasma glucose levels were measured at 10 min intervals, the insulin derivative to be tested and human insulin (one dose level per rat, n=6-7 per dose level) were infused (i.v.) at a constant rate for 300 min. Plasma glucose levels were measured at 10 min intervals throughout and infusion of 20% aqueous glucose was adjusted accordingly in order to maintain euglyceamia. Samples of re-suspended erythrocytes were pooled from each rat and returned in about ½ ml volumes via the carotid catheter.

On each experimental day, samples of the solutions of the individual insulin derivatives to be tested and the human insulin solution were taken before and at the end of the clamp experiments and the concentrations of the peptides were confirmed by HPLC. Plasma concentrations of rat insulin and C-peptide as well as of the insulin derivative to be tested and human insulin were measured at relevant time points before and at the end of the studies. Rats were killed at the end of experiment using a pentobarbital overdose.

Example 24

Pulmonary Delivery of Insulin Derivatives to Rats

The test substance will be dosed pulmonary by the drop instillation method. In brief, male Wistar rats (app. 250 g) are anaesthesized in app. 60 ml fentanyl/dehydrodenzperidol/-dormicum given as a 6.6 ml/kg sc priming dose and followed by 3 maintenance doses of 3.3 ml/kg sc with an interval of 30 min. Ten minutes after the induction of anaesthesia, basal samples are obtained from the tail vein (t=−20 min) followed by a basal sample immediately prior to the dosing of test substance (t=0). At t=0, the test substance is dosed intra tracheally into one lung. A special cannula with rounded ending is mounted on a syringe containing the 200 ul air and test substance (1 ml/kg). Via the orifice, the cannula is introduced into the trachea and is forwarded into one of the main bronchi—just passing the bifurcature. During the insertion, the neck is palpated from the exterior to assure intratracheal positioning. The content of the syringe is injected followed by 2 sec pause. Thereafter, the cannula is slowly drawn back. The rats are kept anaesthetized during the test (blood samples for up to 4 or 8 hrs) and are euthanized after the experiment.

The invention claimed is:

1. An insulin derivative comprising a parent insulin and a substituent, wherein the substituent is attached either to an ε-amino group of a Lys residue present in the A-chain of the parent insulin at position A8, A9, A10, A12, A14, A15, A17, A18, A21, A22, A23 or A24 or to an ε-amino group of a Lys residue in the B-chain of the parent insulin at position B1, B2, B4, B20, B21 or B22, wherein said insulin derivative has a prolonged profile of action.

2. The insulin derivative according to claim 1, wherein the substituent is a lipophilic group containing from 4 to 40 carbon atoms.

3. The insulin derivative according to claim 1, wherein the substituent comprises an acyl group having from 6 to 40 carbon atoms.

4. The insulin derivative according to claim 1, wherein the substituent comprises an acyl group having from 12 to 36 carbon atoms.

5. The insulin derivative according to claim 1, wherein the substituent comprises the acyl group $CH_3$—$(CH_2)_n$—CO—, where $4 \leq n \leq 38$.

6. The insulin derivative according to claim 1, wherein the substituent comprises the acyl group (COOH)—$(CH_2)_n$—CO—, where $4 \leq n \leq 38$.

7. The insulin derivative according to claim 1, wherein the substituent comprises the acyl group ($NH_2$—CO)—$(CH_2)_n$—CO—, where $4 \leq n \leq 38$.

8. The insulin derivative according to claim 1, wherein the substituent comprises the acyl group HO—$(CH_2)_n$—CO—, where $4 \leq n \leq 38$.

9. The insulin derivative according to claim 1, wherein the substituent comprises the acyl group 5-α lithocholic acid or 5-β lithocholic acid.

10. The insulin derivative according to claim 1, wherein the substituent comprises the acyl group is selected from the group consisting of 5-α or 5-β isomers of cholic acid, hyocholic acid, deoxycholic acid, chenodeoxycholic acid, ursodeoxycholic acid, hyodeoxycholic acid and cholanic acid.

11. The insulin derivative according to claim 1, wherein the substituent comprises the acyl group a 5-α or 5-β isomer of dehydrolithocholic acid.

12. The insulin derivative according to claim 1, wherein the substituent comprises the acyl group is selected from the group consisting of fusidic acid, a fusidic acid derivative and glycyrrhetinic acid.

13. The insulin derivative according to claim 1 where the substituent is of general formula:

—W—X—Y—Z wherein W is:
- an α-amino acid residue having a carboxylic acid group in the side chain which residue forms, with one of its carboxylic acid groups, an amide group with the ε-amino group of a Lys residue present in the A- or the B-chain of the parent insulin; or
- a chain composed of two, three or four α-amino acid residues linked together via amide bonds, which chain, via an amide bond, is linked to the ε-amino group of a Lys residue present in the A- or the B-chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
- a covalent bond from X to the ε-amino group of a Lys residue present in the A- or the B-chain of the parent insulin;

X is:
- —CO—;
- —CH(COOH)CO—;
- —CON(CH$_2$$\overline{\text{C}}$OOH)CH$_2$CO—;
- —CON(CH$_2$COOH)CH$_2$$\overline{\text{C}}$ON(CH$_2$COOH)CH$_2$CO—;
- —CON(CH$_2$CH$_2$COOH)CH$_2$CH$_2$CO—;
- —CON(CH$_2$CH$_2$COOH)CH$_2$CH$_2$$\overline{\text{C}}$ON (CH$_2$CH$_2$COOH)CH$_2$CH$_2$CO—;
- —CONHCH(COOH)(CH$_2$)$_4$$\overline{\text{N}}$HCO—;
- —CON(CH$_2$CH$_2$COOH)CH$_2$C$\overline{\text{O}}$—; or
- —CON(CH$_2$COOH)CH$_2$CH$_2$$\overline{\text{C}}$O—

Provided that
a) when W is an amino acid residue or a chain of amino acid residues, the underscored carbonyl carbon in X forms an amide bond with an amino group in W, or
b) when W is a covalent bond, the underscored carbonyl carbon in X forms an amide bond with the ε-amino group of a Lys residue present in the A- or the B-chain of the parent insulin;

Y is:
- —(CH$_2$)$_m$— where m is an integer in the range of 6 to 32;
- a divalent hydrocarbon chain comprising 1, 2 or 3 —CH═CH— groups and a number of —CH$_2$— groups sufficient to give a total number of carbon atoms in the chain in the range of 10 to 32;
- a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and Z is:
- —COOH;
- —CO-Asp;
- —CO-Glu;
- —CO-Gly;
- —CO-Sar;
- —CH(COOH)$_2$;
- —N(CH$_2$COOH)$_2$;
- —SO$_3$H; or
- —PO$_3$H;

and any $Zn^{2+}$ complexes thereof.

14. The insulin derivative according to claim 13, wherein W is an α-amino acid residue having from 4 to 10 carbon atoms.

15. The insulin derivative according to claim 13, wherein W is a chain composed of two α-amino acid residues of which one has from 4 to 10 carbon atoms and a free carboxylic acid group while the other has from 2 to 11 carbon atoms but no free carboxylic acid group.

16. The insulin derivative according to claim 13, wherein W is a covalent bond.

17. The insulin derivative according to claim 13, wherein X is —CO— or —COCH(COOH)CO—.

18. The insulin derivative according to claim 13, wherein Y is —$(CH_2)_m$— where m is an integer in the range of from 6 to 32.

19. The insulin derivative according to claim 13, wherein Z is —COOH.

20. The insulin derivative according to claim 1, wherein the parent insulin is an insulin analogue.

21. The insulin derivative according to claim 20, wherein the parent insulin is ArgB29 human insulin or ArgB29desB30 human insulin.

22. A zinc complex of an insulin derivative according to claim 1, wherein two zinc ions, three zinc ions, four zinc ions, five zinc ions, six zinc ions, seven zinc ions, eight zinc ions, nine zinc ions, ten six zinc ions, eleven six zinc ions or twelve six zinc ions are bound per six molecules of insulin derivative.

23. A method for producing a pharmaceutical composition according to claim 22, wherein up to about 12 zinc ions per 6 molecules of insulin derivative are added to the pharmaceutical composition.

24. A pharmaceutical composition for the treatment of diabetes in a patient in need of such treatment, comprising a therapeutically effective amount of an insulin derivative according to claim 1, optionally together with a pharmaceutically acceptable carrier.

25. A method for producing a pharmaceutical composition according to claim 1, wherein up to about 12 zinc ions per 6 molecules of insulin derivative are added to the pharmaceutical composition.

26. A method of treating diabetes in a patient in need of such a treatment, comprising administering to the patient a therapeutically effective amount of an insulin derivative according to claim 1, optionally together with a pharmaceutically acceptable carrier.

27. A method according to claim 26 for pulmonary treatment of diabetes.

28. A mixture of an insulin derivative according to claim 1, and a rapid acting insulin analogue selected from the group consisting of AspB28 human insulin; LysB28ProB29 human insulin and LysB3GluB29 human insulin.

29. The insulin derivative according to claim 1, wherein the insulin derivative is selected from the group consisting of
$N^{\epsilon A9}$-myristyl LysA9 ArgB29 desB30 human insulin,
$N^{\epsilon B22}$-myristyl LysB22 ArgB29 desB30 human insulin,
$N^{\epsilon A15}$-myristyl LysA15 ArgB29 desB30 human insulin,
$N^{\epsilon A18}$-myristyl LysA18 ArgB29 desB30 human insulin,
$N^{\epsilon A22}$-myristyl LysA22 ArgB29 desB30 human insulin,
$N^{\epsilon A9}$-ω-carboxypentadecanoyl-γ-Glu LysA9 ArgB29 desB30 human insulin,
$N^{\epsilon B22}$-ω-carboxypentadecanoyl-γ-Glu LysB22 ArgB29 desB30 human insulin,
$N^{\epsilon A15}$-ω-carboxypentadecanoyl-γ-Glu LysA15 ArgB29 desB30 human insulin,
$N^{\epsilon A18}$-ω-carboxypentadecanoyl-γ-Glu LysA18 ArgB29 desB30 human insulin,
$N^{\epsilon A22}$-ω-carboxypentadecanoyl-γ-Glu LysA22 ArgB29 desB30 human insulin.

* * * * *

UNITED STATES PATENT AND TRADEMARK OFFICE
CERTIFICATE OF CORRECTION

| | | |
|---|---|---|
| PATENT NO. | : 8,722,620 B2 | Page 1 of 1 |
| APPLICATION NO. | : 12/280851 | |
| DATED | : May 13, 2014 | |
| INVENTOR(S) | : Fynbo et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 512 days.

Signed and Sealed this
Twenty-eighth Day of July, 2015

Michelle K. Lee
*Director of the United States Patent and Trademark Office*